United States Patent
Cheshnovsky et al.

(10) Patent No.: US 10,088,418 B2
(45) Date of Patent: Oct. 2, 2018

(54) METHOD AND SYSTEM FOR MICROSCOPY

(71) Applicant: Ramot at Tel-Aviv University Ltd., Tel-Aviv (IL)

(72) Inventors: Ori Cheshnovsky, RaAnana (IL); Omer Tzang, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 77 days.

(21) Appl. No.: 15/329,260

(22) PCT Filed: Sep. 2, 2015

(86) PCT No.: PCT/IL2015/050882
§ 371 (c)(1),
(2) Date: Jan. 26, 2017

(87) PCT Pub. No.: WO2016/035075
PCT Pub. Date: Mar. 10, 2016

(65) Prior Publication Data
US 2017/0219489 A1 Aug. 3, 2017

Related U.S. Application Data

(60) Provisional application No. 62/044,458, filed on Sep. 2, 2014.

(51) Int. Cl.
*G01J 3/46* (2006.01)
*G01N 21/63* (2006.01)
(Continued)

(52) U.S. Cl.
CPC ....... *G01N 21/636* (2013.01); *G01N 21/1717* (2013.01); *G01N 21/65* (2013.01); *G02B 21/06* (2013.01); *G01N 2021/1731* (2013.01)

(58) Field of Classification Search
CPC ............ G01N 21/1717; G01N 21/636; G01N 21/1731; G01N 2021/1714; G01N 21/65; G01N 25/00
See application file for complete search history.

(56) References Cited

U.S. PATENT DOCUMENTS

| | | | |
|---|---|---|---|
| 4,652,757 A | 3/1987 | Carver | |
| 5,748,317 A | 5/1998 | Maris et al. | |
| (Continued) | | | |

FOREIGN PATENT DOCUMENTS

| | | |
|---|---|---|
| WO | WO 2013/007726 | 1/2013 |
| WO | WO 2016/035075 | 3/2016 |

OTHER PUBLICATIONS

Y. Ezzahri, "Application of network identification by deconvolution method to the thermal analysis of the pump-probe transient thermoreflectance signal", 2009, Review of Scientific Instruments, p. 1-13.*
(Continued)

*Primary Examiner* — Dominic J Bologna
*Assistant Examiner* — Maurice Smith

(57) ABSTRACT

A method of microscopy is disclosed. The method comprises directing a pulse of a pump optical beam to form an optical spot on a substance and measuring changes in a temperature-dependent or photo-excited property of the substance. The method further comprises analyzing the measured changes to distinguish between information pertaining to the property at a portion of the spot, and information pertaining to the property at other portions of the spot. A largest diameter of the portion of the spot is optionally and preferably less than a central wavelength of the pump optical beam.

29 Claims, 19 Drawing Sheets
(15 of 19 Drawing Sheet(s) Filed in Color)

(51) Int. Cl.
*G01N 21/17* (2006.01)
*G01N 21/65* (2006.01)
*G02B 21/06* (2006.01)

(56) References Cited

U.S. PATENT DOCUMENTS

| | | | | |
|---|---|---|---|---|
| 2003/0150993 | A1* | 8/2003 | Nicolaides | G01N 21/171 250/339.11 |
| 2007/0023686 | A1 | 2/2007 | Wolleschensky et al. | |
| 2013/0134310 | A1 | 5/2013 | Furstenberg et al. | |
| 2013/0162994 | A1* | 6/2013 | Xie | G01N 21/171 356/342 |
| 2015/0110150 | A1* | 4/2015 | Schmidt | G01N 21/1717 374/43 |

OTHER PUBLICATIONS

Zharov, Vladimir, "Photothermal guidance for selective photothermolysis with nanoparticles", 2004, SPIE, p. 291-98.*

International Search Report and the Written Opinion dated Dec. 30, 2015 From the International Searching Authority Re. Application No. PCT/IL2015/050882.

Supplementary European Search Report and the European Search Opinion dated Mar. 26, 2018 From the European Patent Office Re. Application No. 15837541.0. (13 Pages).

Danielli et al. "Label-Free Photoacoustic Nanoscopy", Journal of Biomedical Optics, XP060047527, 19(8): 086006-1-086006-10, Published Online Aug. 7, 2014. Abstract, p. 3, Fig.1.

Nedosekin et al. "Super-Resolution Nonlinear Photothermal Microscopy", Small, XP055458548, 10(1): 135-142, Jan. 15, 2014. Abstract, p. 136, Fig.1.

Sreekumar et al. "Dual Phase Wide Band Lock-in Amplifier for Linear and Non-Linear Photo-Thermal Signal Processing", Indian Journal of Pure & Applied Physics, XP055459055, 42(4): 258-264, Apr. 2004. Abstract, p. 260, 1-h Col., Last Para.

Tzang et al. "Super-Resolution in Label-Free Photomodulated Refelctivity", Nano Letters, XP055458317, 15(2): 1362-1367, Jan. 20, 2015. Abstract, p. 1363-1364, p. 1365, r-h Col.—p. 1366, 1-h Col.

Velinov et al. "Far Field Resolution Beyond the Abbe Limit Using Photodiffraction", Journal of Microscopy, XP055459065, 193(Pt.2): 142-149, Feb. 1999. Abstract, p. 145, r-h Col.—p. 147, p. 148, r-h Col., Fig.4.

Wang et al. "Far-Field Imaging of Non-Fluorescent Species With Subdiffraction Resolution", Nature Photonics, XP055458529, 7(6): 449-453, Published Online Apr. 28, 2013. Abstract, p. 449, 452, r-h Col., Figs. 1, 2.

\* cited by examiner

METHOD AND SYSTEM FOR MICROSCOPY

RELATED APPLICATIONS

This application is a National Phase of PCT Patent Application No. PCT/IL2015/050882 having International filing date of Sep. 2, 2015, which claims the benefit of priority under 35 USC § 119(e) of U.S. Provisional Patent Application No. 62/044,458 filed Sep. 2, 2014. The contents of the above applications are all incorporated herein by reference in their entirety.

FIELD AND BACKGROUND OF THE INVENTION

The present invention, in some embodiments thereof, relates to microscopy and, more particularly, but not exclusively, microscopy based on changes induced by interaction of a substance with an optical beam.

Optical microscopy has succeeded to surpass the Abbe resolution limit (about 0.5λ) either by near field techniques [1], or by far field super-resolution (SR) techniques such as stimulated emission depletion (STED), photo-activated localization microscopy (PALM), stochastic optical reconstruction microscopy (STORM) saturable absorption (SAX), structured illumination, SR optical fluctuation imaging (SOFI), and quantum emitters microscopy [2-9]. Fluorescence based techniques are useful when functional groups can be reliably and selectively labeled.

Also known are methods which are free of fluorescent labeling. Wang and coworkers used ground state depletion of the charge carriers in graphene-like structures in transmission mode [10]. Nedosekin and coworkers use nonlinear photo thermal microscopy in fluid medium [11]. Fleischer and coworkers generalized the Abbe's theory of diffraction to include nonlinear propagation and resolution enhancement [12,13].

SUMMARY OF THE INVENTION

According to an aspect of some embodiments of the present invention there is provided a method of microscopy. The method comprises directing a pulse of a pump optical beam to form an optical spot on a substance; measuring changes in a temperature-dependent or photo-excited property of the substance; and analyzing the measured changes to distinguish between information pertaining to the property at a portion of the spot, and information pertaining to the property at other portions of the spot.

According to an aspect of some embodiments of the present invention there is provided a system of microscopy. The system comprises an optical system configured for directing a pulse of a pump optical beam to form an optical spot on a substance; a measuring system configured for measuring changes in a temperature-dependent or photo-excited property of the substance; and an analysis system configured for analyzing the measured changes to distinguish between information pertaining to the property at a portion of the spot, and information pertaining to the property at other portions of the spot.

According to some embodiments of the invention the pump optical beam is selected to induce nonlinear excitation in the substance.

According to some embodiments of the invention the pump optical beam has a pulse duration of less than 100 ps and energy above 100 pJ.

According to some embodiments of the invention a spectral region of interest is selected so as to measure changes induced by non-linear excitation in the substance.

According to some embodiments of the invention the measurement comprises detecting changes induced by the pump beam, and applying threshold to the detected changes such as to filter out changes induced by the other portions of the spot.

According to some embodiments of the invention the pump optical beam is modulated.

According to some embodiments of the invention the measurement comprises detecting the changes at a frequency which is an nth harmonic of the modulation, n being at least 2.

According to some embodiments of the invention the measurement is by a pulse of a probe optical beam.

According to any embodiments of the invention, a largest diameter of the portion of the spot is less than the central wavelength of the probe optical beam. According to any embodiments of the invention, a largest diameter of the portion of the spot is less than less than half or less than 0.4 or less than 0.35 or less than 0.3 or less than 0.25 of the central wavelength of the probe optical beam.

According to some embodiments of the invention the measurement is executed electrically.

According to some embodiments of the invention a time delay between the probe pulse and the pump pulse is less than 10 ps. According to some embodiments of the invention the time delay between the probe pulse and the pump pulse is about 1 ps or less. According to some embodiments of the invention the time delay between the probe pulse and the pump pulse is from about 100 fs to about 10 ps, or from about 100 fs to about 9 ps, or from about 100 fs to about 8 ps, or from about 100 fs to about 7 ps, or from about 100 fs to about 6 ps, or from about 100 fs to about 5 ps, or from about 100 fs to about 4 ps, or from about 100 fs to about 3 ps, or from about 100 fs to about 2 ps, or from about 100 fs to about 1 ps or less.

According to some embodiments of the invention a ratio between central wavelengths of the probe and the pump optical beams is an integer. According to some embodiments of the invention a ratio between wavelengths of the probe optical beam and the pump optical beam equals 2.

According to some embodiments of the invention the probe optical beam and the pump optical beam are generated by the same source, but are directed to the substance via different optical paths.

According to any embodiments of the invention, a largest diameter of the portion of the spot is less than the central wavelength of the pump optical beam. According to any embodiments of the invention, a largest diameter of the portion of the spot is less than less than half or less than 0.4 or less than 0.35 or less than 0.3 or less than 0.25 of the central wavelength of the pump optical beam.

According to some embodiments of the invention the temperature-dependent property comprises at least thermoreflectance.

According to some embodiments of the invention the temperature-dependent property comprises at least luminescence.

According to some embodiments of the invention the temperature-dependent property comprises at least a Raman shift.

According to some embodiments of the invention the temperature-dependent property comprises at least optical absorption.

According to some embodiments of the invention the temperature-dependent property comprises at least optical emission.

According to some embodiments of the invention the temperature-dependent property comprises at least black-body radiation.

According to some embodiments of the invention the substance is inorganic. According to some embodiments of the invention the substance is organic.

According to some embodiments of the invention the substance is not functionally labeled.

According to some embodiments of the invention the substance is solid.

According to some embodiments of the invention the substance is dry. According to some embodiments of the invention the substance is wet.

According to some embodiments of the invention the method is executed in vacuum. According to some embodiments of the invention the method is executed in gaseous environment. According to some embodiments of the invention the method is executed in liquid environment.

According to some embodiments of the invention the substance has a thickness of at least 0.1 nm.

According to some embodiments of the invention the substance is opaque to the pump optical beam.

According to some embodiments of the invention an absorption thickness of the substance to the pump optical beam is at most 10 micron.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a system for microscopy, according to some embodiments of the present invention;

FIG. 2 is a schematic illustration showing a view of a substance and an optical spot formed thereon;

FIG. 3 is a flowchart diagram of a method of microscopy, according to some embodiments of the present invention;

Figure 5:
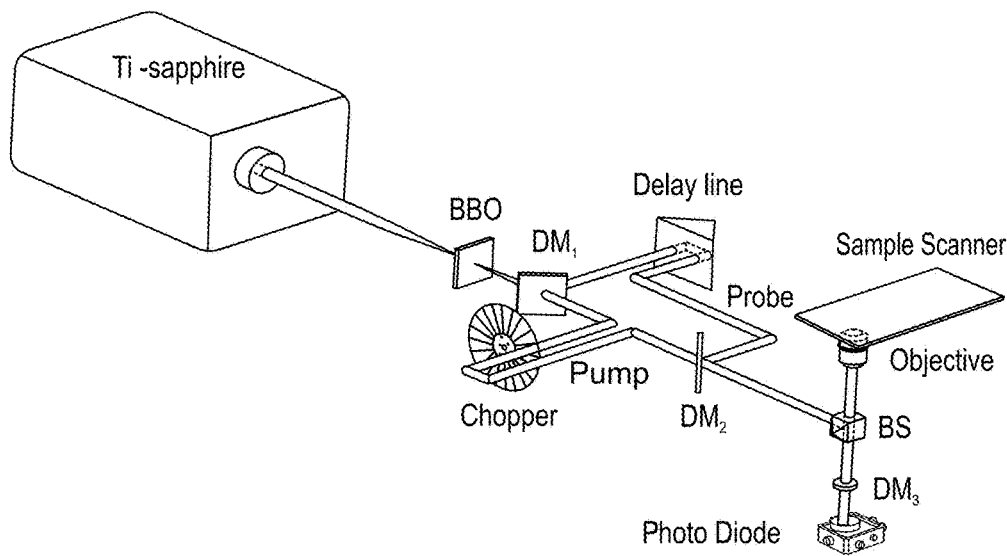
Figure 7A:
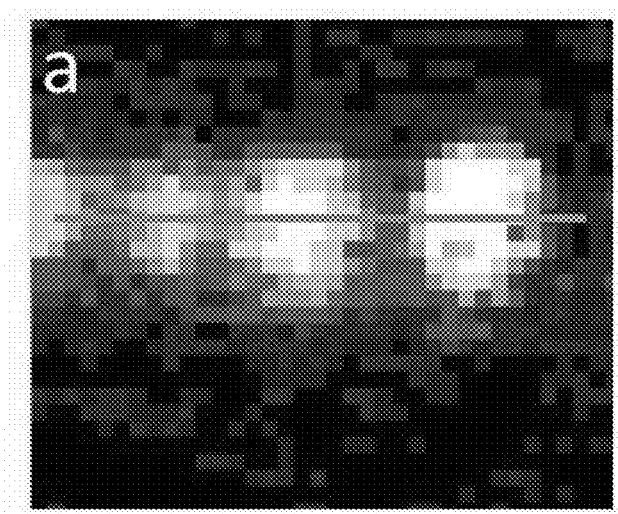
Figure 7B:
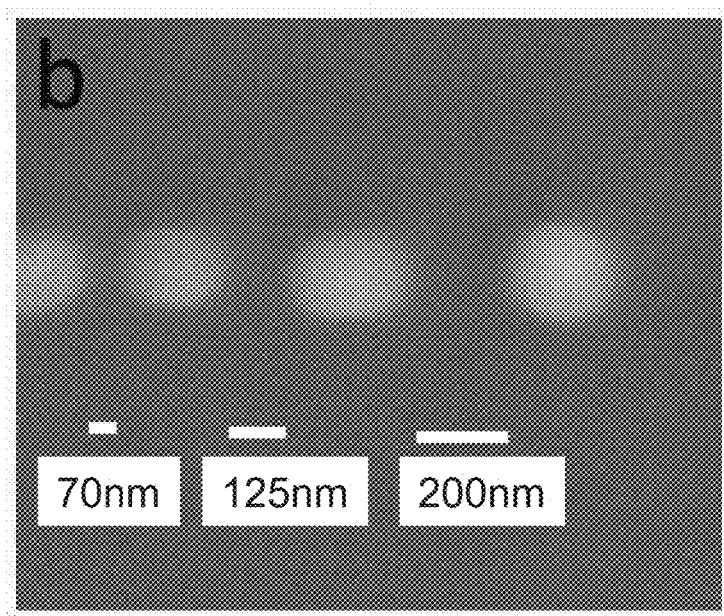
Figure 7C:
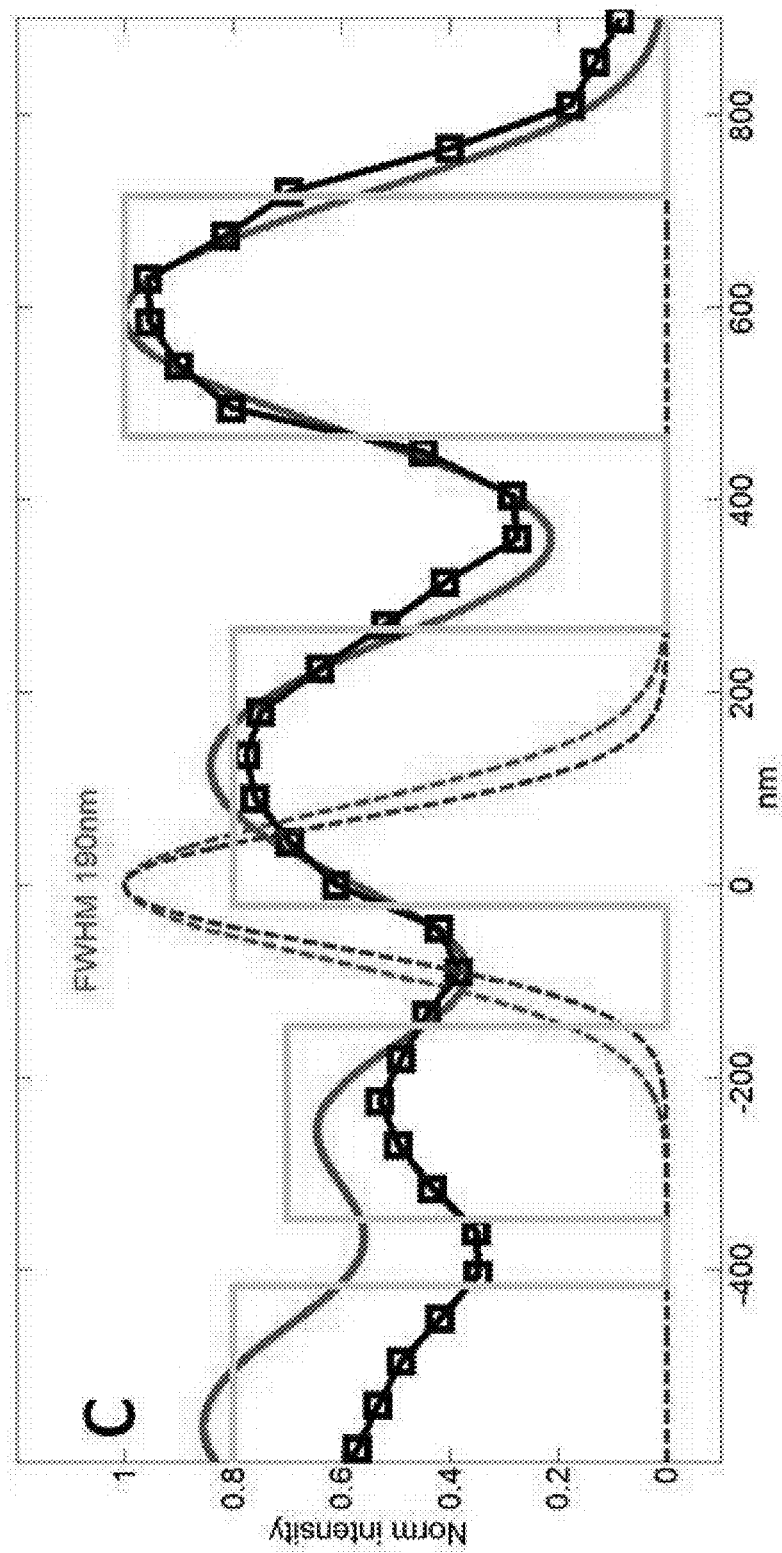
Figures 8A, 8B:
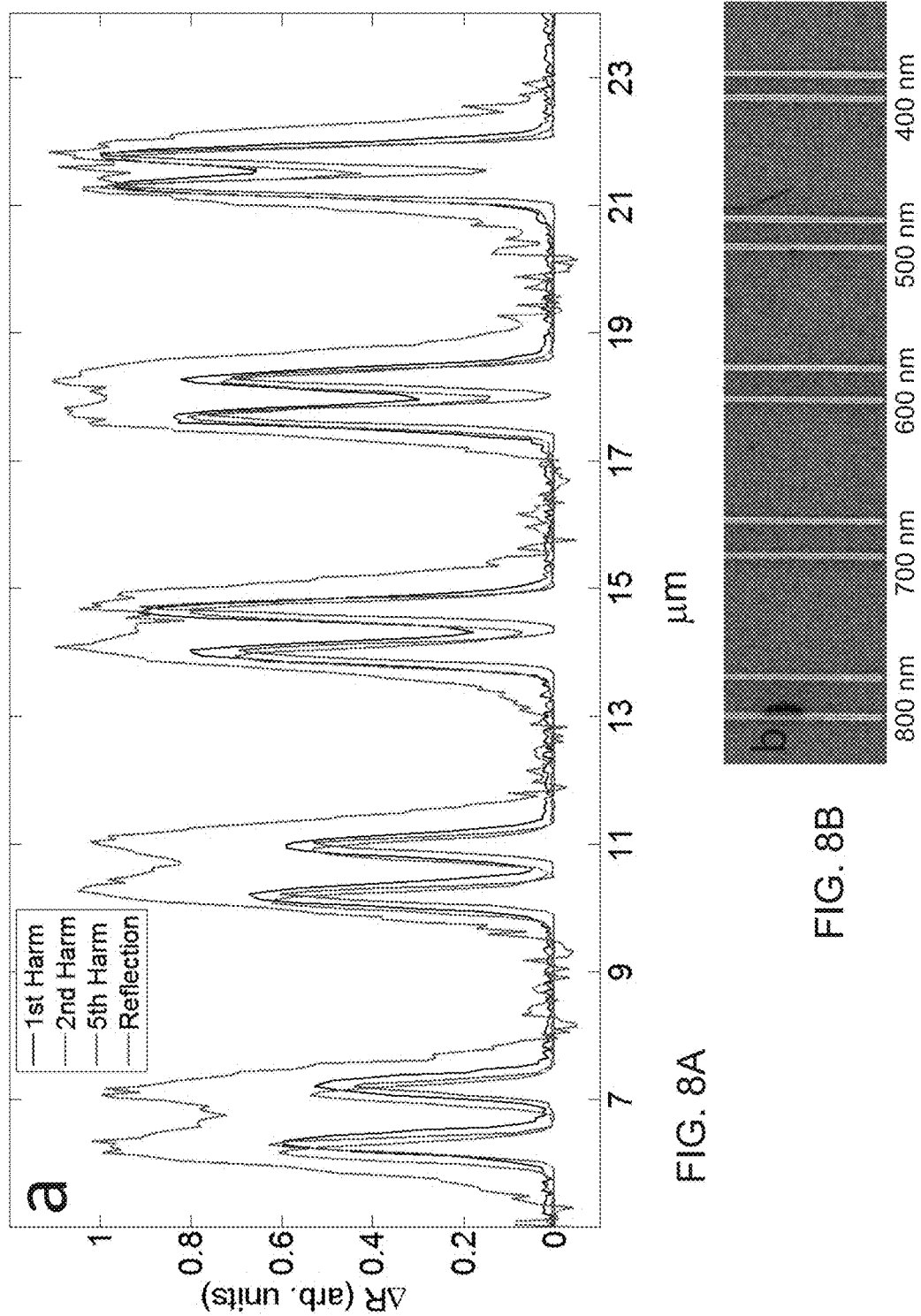
Figure 8C:
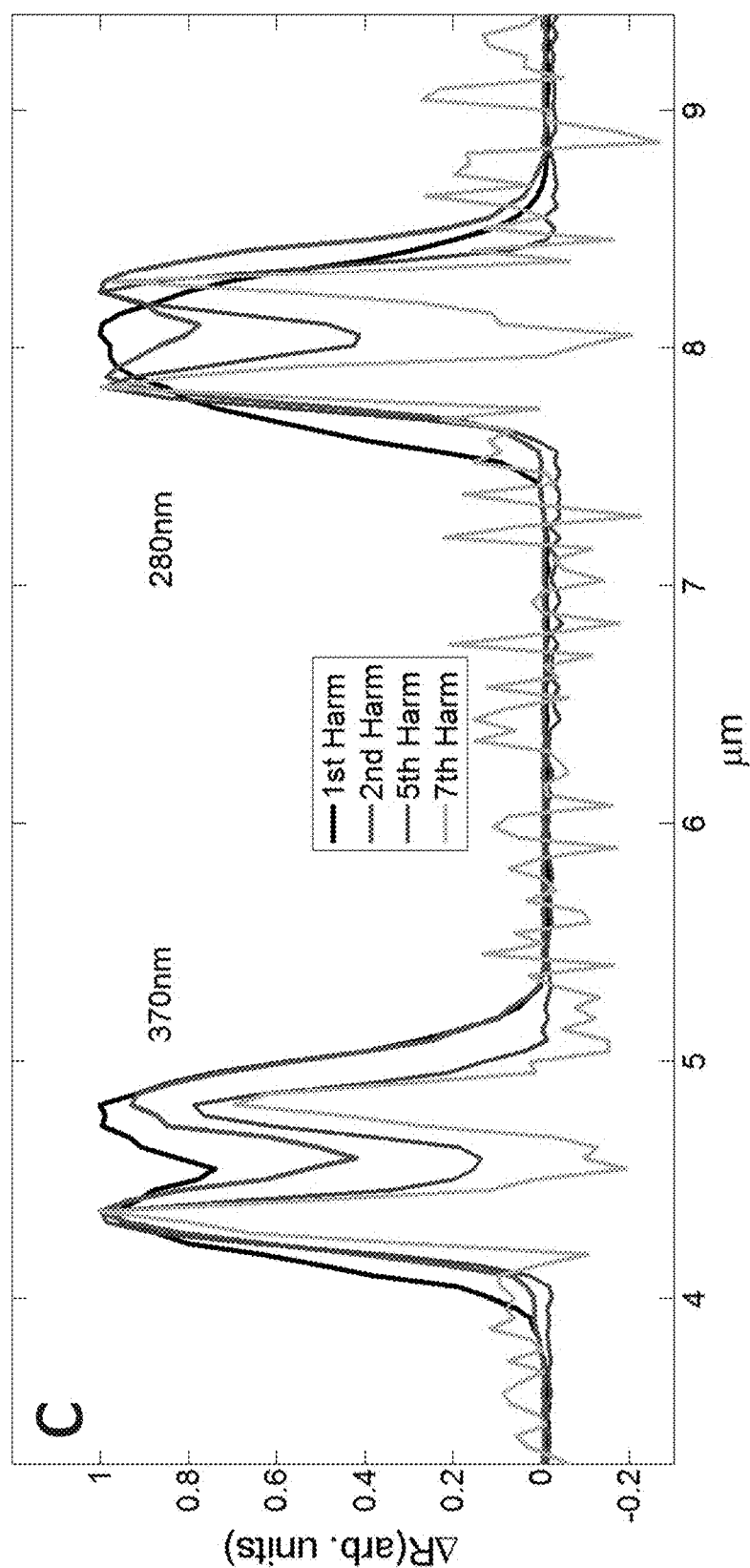
Figure 9:
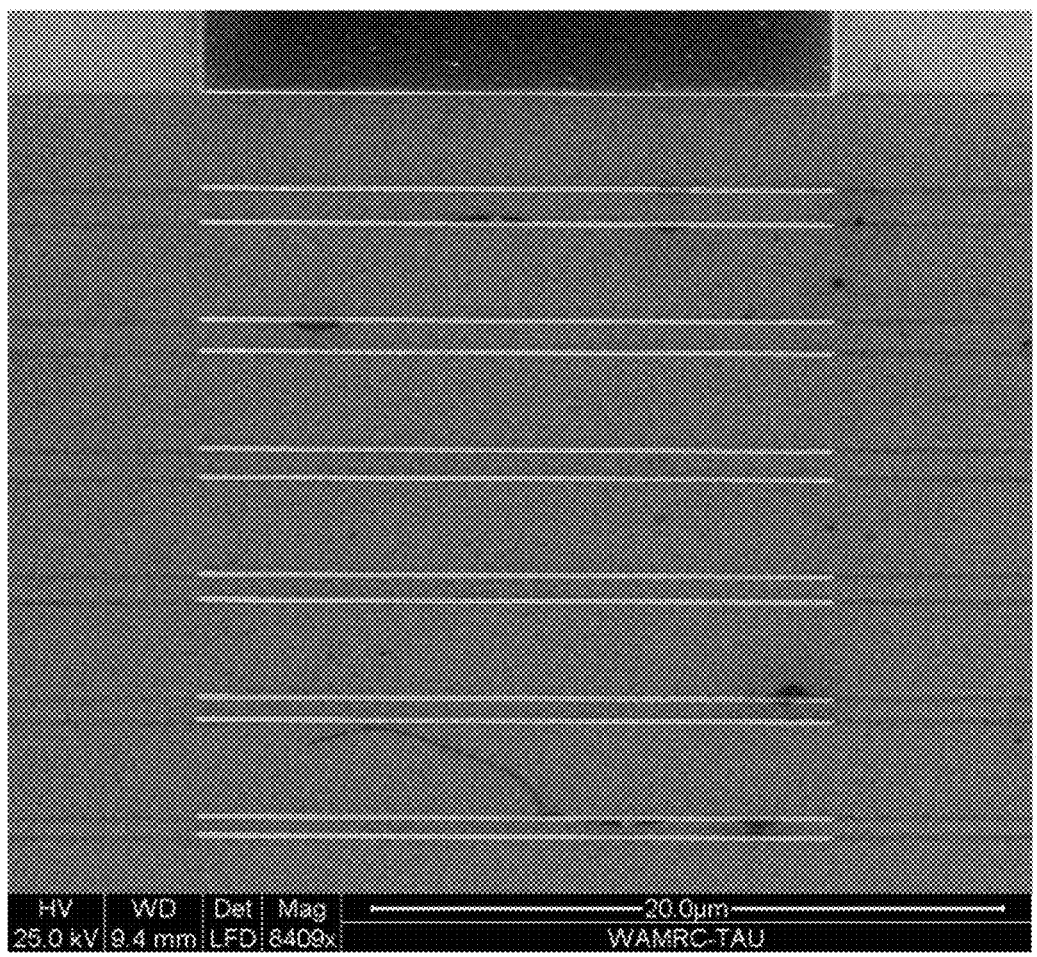
Figure 10:
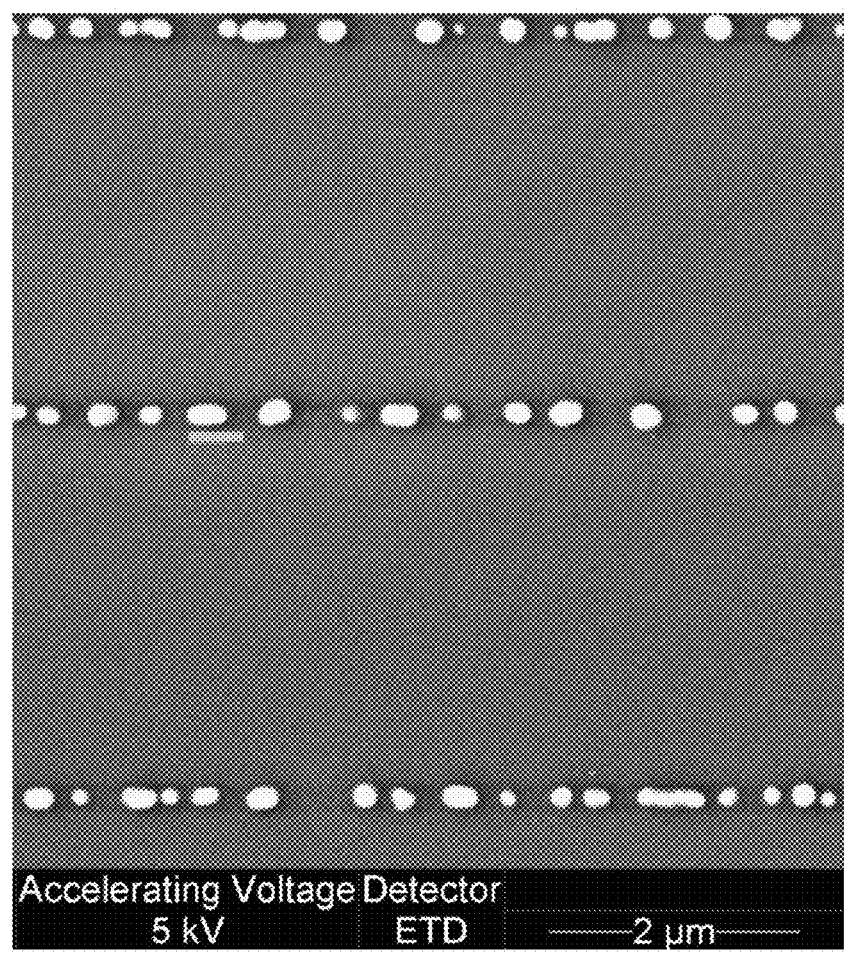
Figure 11A:
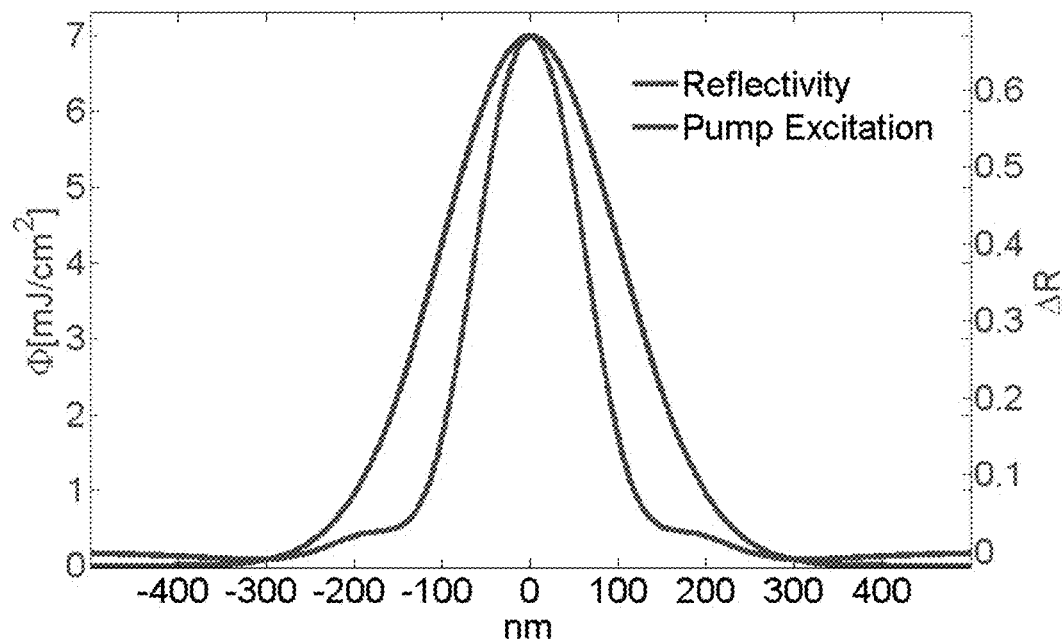
Figure 11B:
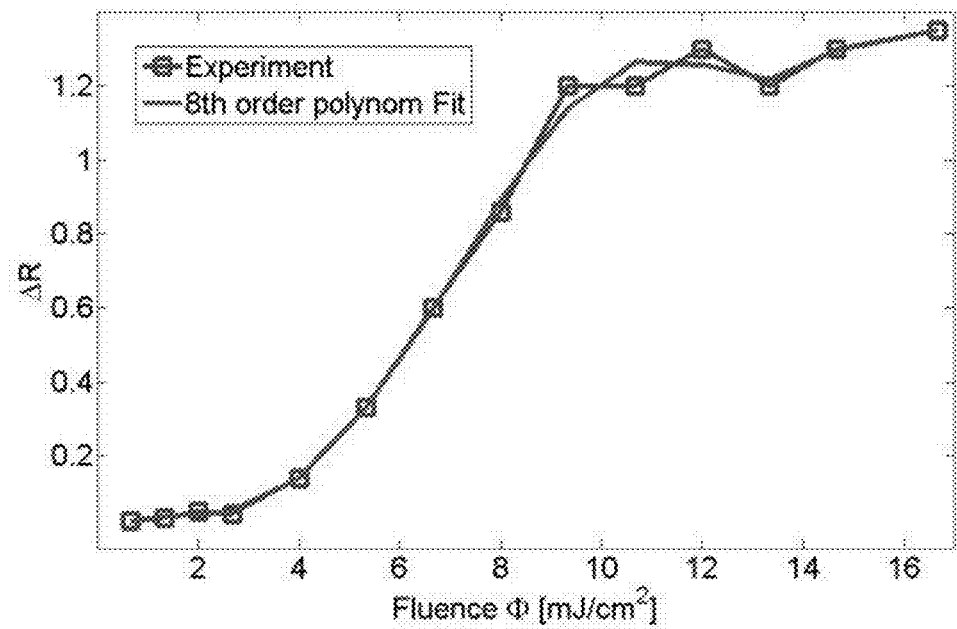
Figure 12:
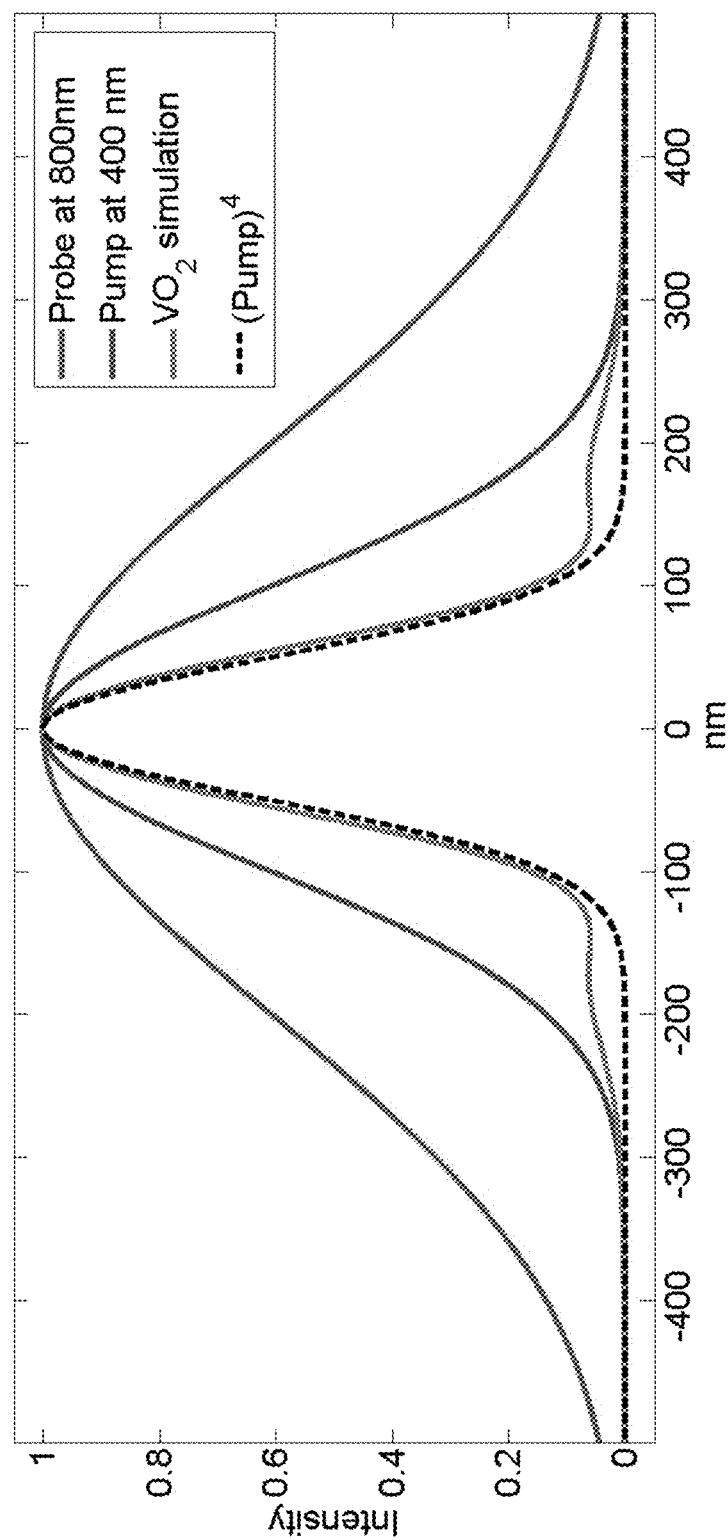
Figure 13:
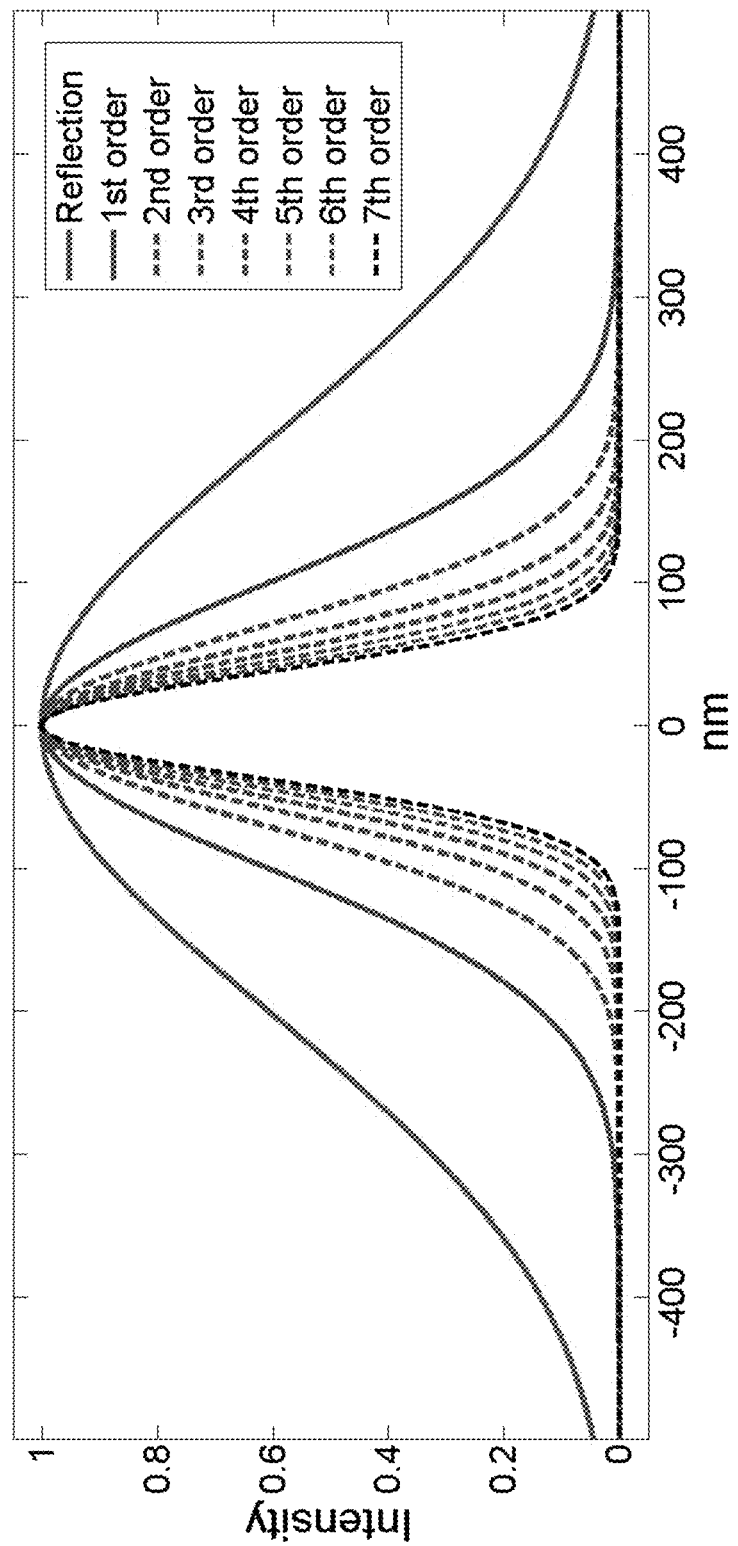
Figure 14:
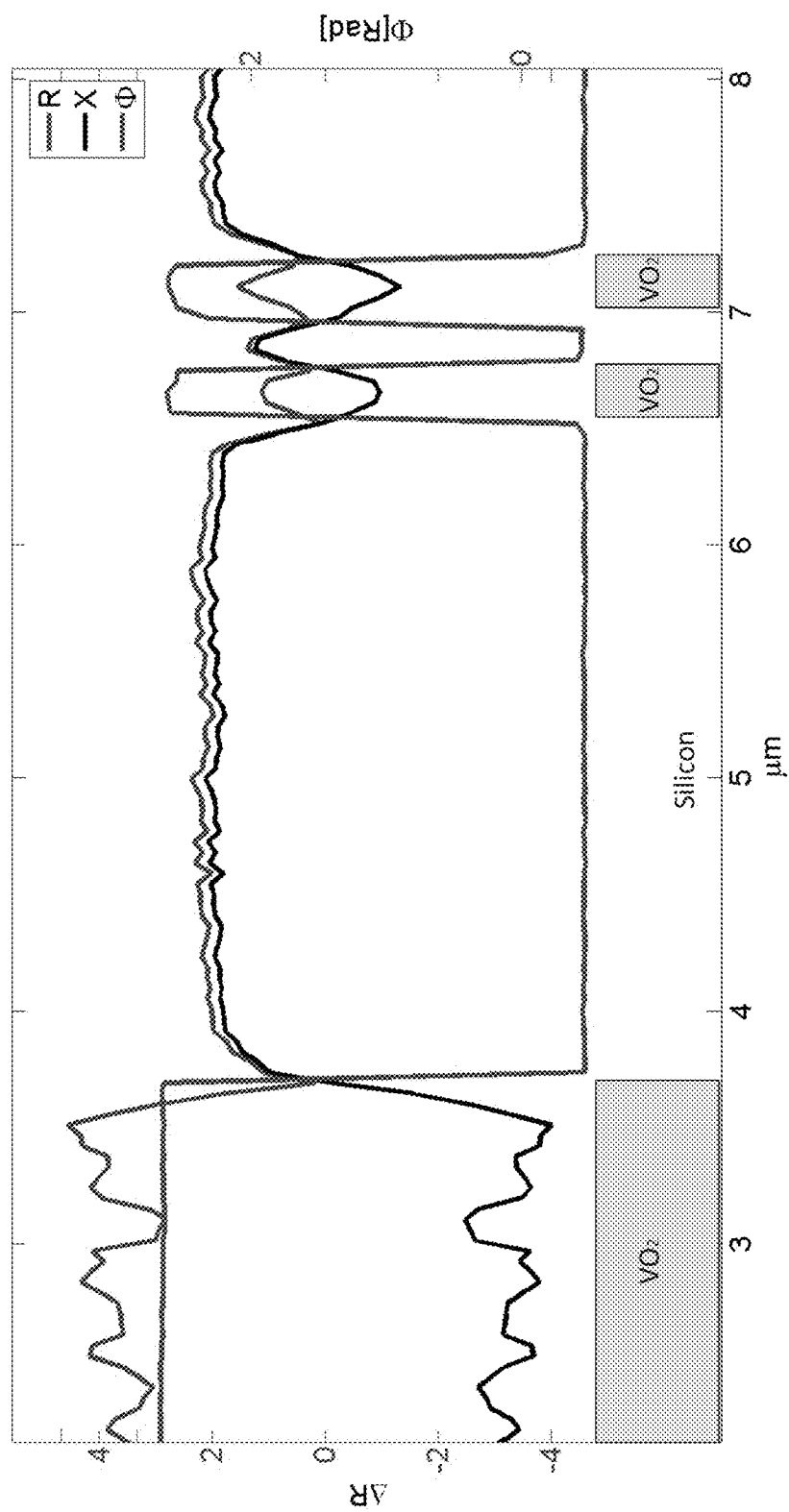
Figure 15:
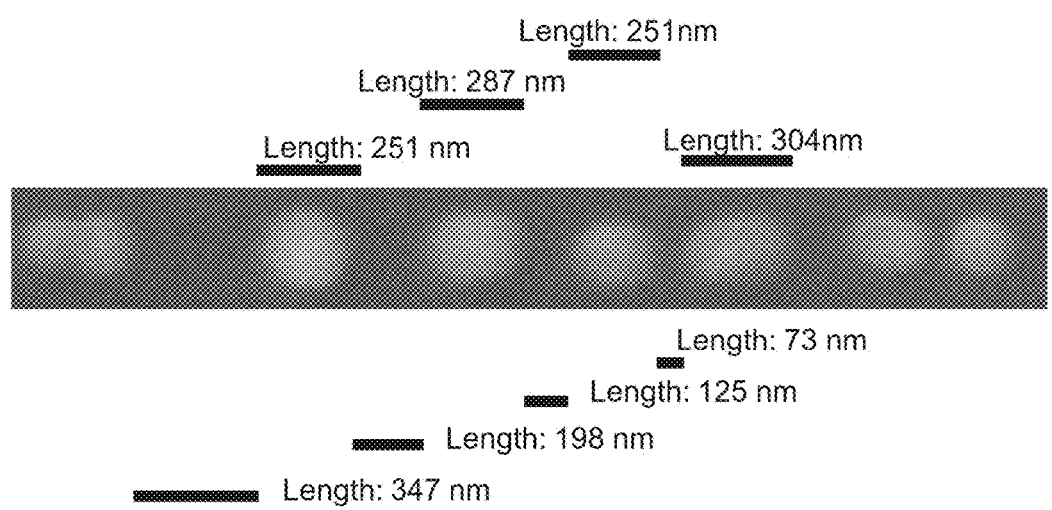
Figure 16:
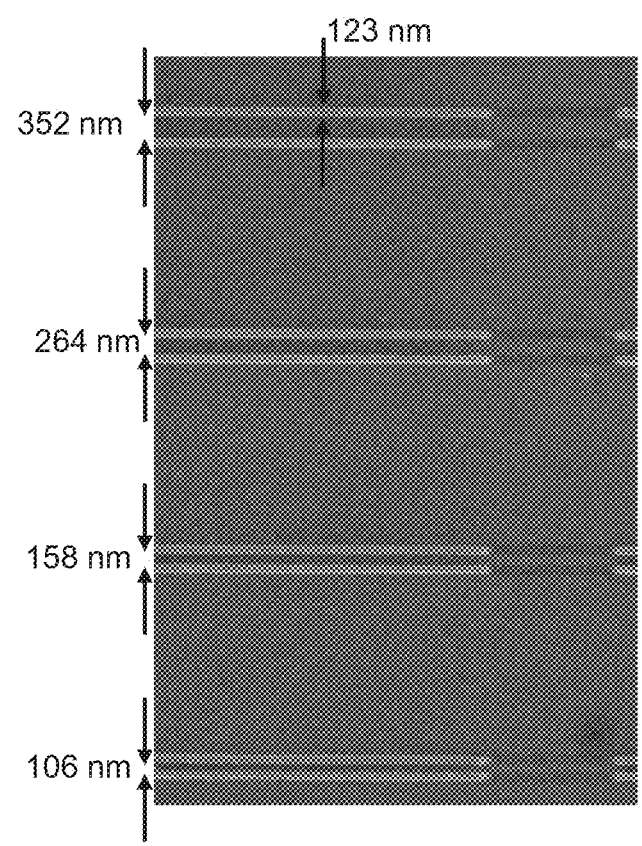
Figure 17:
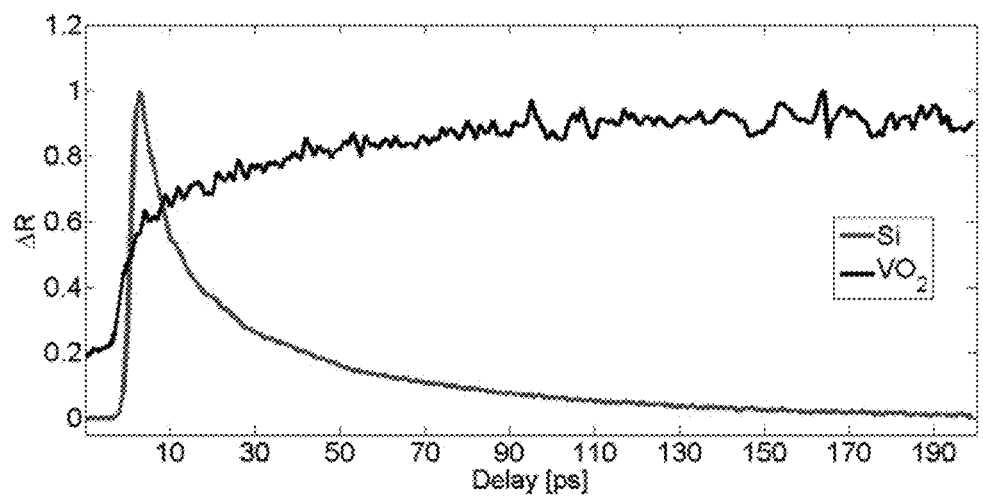

FIGS. 4A-D illustrate an SR technique employed in experiments performed according to some embodiments of the present invention;

FIG. 5 is a schematic illustration of a thermoreflectance experimental setup used in experiments performed according to some embodiments of the present invention;

FIGS. 6A-E show thermoreflectance characterization of a single $VO_2$ particle, as obtained in experiments performed according to some embodiments of the present invention;

FIGS. 7A-C show results obtained from several $VO_2$ nanoparticles as obtained in experiments performed according to some embodiments of the present invention;

FIGS. 8A-C show results obtained during experiments performed in accordance with some embodiments of the present invention on silicon layers patterned on sapphire;

FIG. 9 is a SEM image of silicon on sapphire sample, obtained during experiments performed according to some embodiments of the present invention;

FIG. 10 is a SEM image of a $VO_2$ sample, obtained during experiments performed according to some embodiments of the present invention;

FIGS. 11A and 11B show results of simulation of $VO_2$ PSF performed according to some embodiments of the present invention;

FIG. 12 shows simulated profiles effective PSFs of $VO_2$, obtained during experiments performed according to some embodiments of the present invention;

FIG. 13 shows simulated profiles of effective PSFs on a lateral axis, obtained during experiments performed according to some embodiments of the present invention;

FIG. 14 shows line scan of patterned $VO_2$ on silicon, obtained during experiments performed according to some embodiments of the present invention;

FIG. 15 is a SEM image showing input to simulations performed according to some embodiments of the present invention for $VO_2$ particles;

FIG. 16 is a SEM image showing input to simulations performed according to some embodiments of the present invention for silicon pattern on sapphire; and FIG. 17 shows time resolved reflectance of silicon and $VO_2$, obtained during experiments performed according to some embodiments of the present invention.

DESCRIPTION OF SPECIFIC EMBODIMENTS OF THE INVENTION

The present invention, in some embodiments thereof, relates to microscopy and, more particularly, but not exclusively, microscopy based on changes induced by interaction of a substance with an optical beam.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
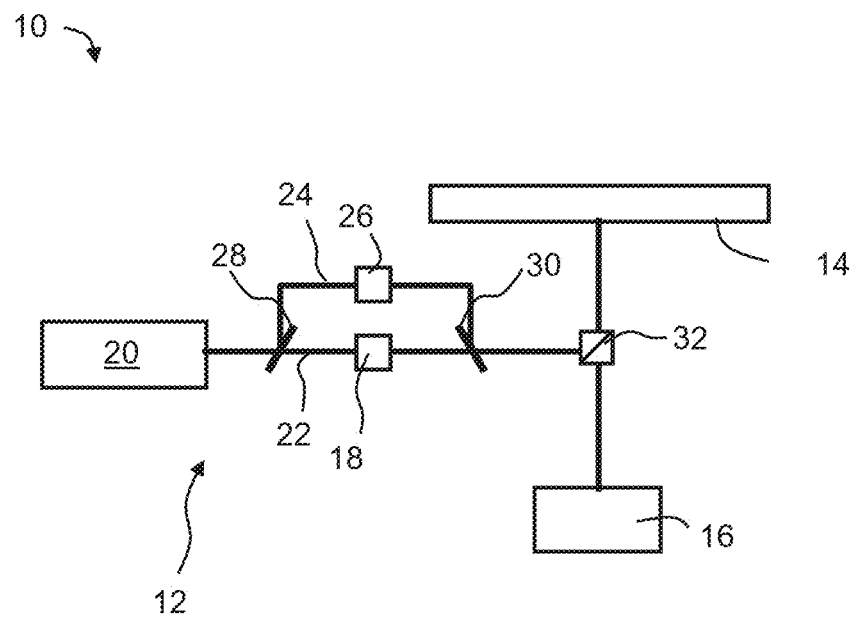
Figure 2:
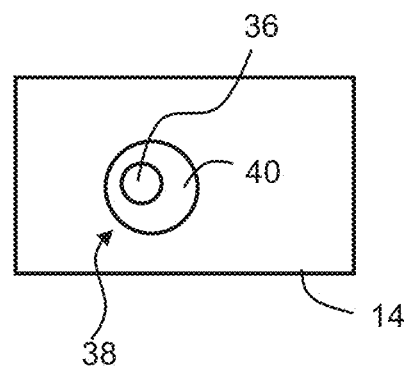

Referring now to the drawings, FIG. 1 is a schematic illustration of a system 10 for microscopy, according to some embodiments of the present invention. System 10 comprises an optical system 12 having a light source 20. Light source 20 generates a pulse of a pump optical beam 22 and system 12 directs the optical beam 22 to form an optical spot on a substance 14. FIG. 2 illustrates a view of substance 14 and an optical spot 38 formed by optical system 12.

As will be explain below, the technique of the present embodiments does not depend on the type and state of the substance. Thus, the substance can be of any type and state, including, without limitation, an inorganic substance, an organic substance, a solid substance, a dry substance, a wet substance, etc. According to some embodiments of the present invention the substance does not comprise a label. According to some embodiments of the present invention the substance is not functionally labeled. According to some embodiments of the present invention the substance does not comprise a heterologous label.

The term "label" as used herein refers to a compound or composition which is conjugated or fused directly or indirectly to the substance and facilitates detection of the substance. The label itself may be detectable (e.g., fluorescent labels) or, in the case of an enzymatic label, may catalyze chemical alteration of the substance which is detectable.

Thus, the present embodiments relate to a substance that is detected by the microscopy without being conjugated or fused to any type of label.

System 10 can operate in vacuum or in a fluidic environment, which can be a gaseous environment (e.g., air) or liquid environment.

Advancements in the semiconductor industry have converged on developing submicron geometric devices for microelectronic circuits. Semiconductor fabrication processes, in their infancy, were sometimes plagued with fatal defectivity that inhibited the production of integrated circuits. As semiconductor fabrication processes became more advanced, the level and occurrence of defects in semiconductor devices have decreased. However, the reduction of semiconductor geometries to submicron levels has manifested inherent defect modes which may impact the performance of resulting semiconductor devices. Silicon wafers provide a common substrate used to fabricate multiple semiconductor devices. As geometries for semiconductor devices are reduced, the inherent characteristics of the device's materials such as silicon become a significant factor. Structural defects are one of the inherent problems facing the advancement of submicron semiconductor devices. Some structural defects negatively impact device performance and may effect, for example, leakage currents, carrier lifetimes, and gate oxide integrity. The technique of the present embodiments is suitable, particularly, but not exclusively, for the characterization of semiconductor and optoelectronic systems in any environment.

The system of the present embodiments is particularly useful for microscopy of relatively thick samples. Typically, but not necessarily substance 14 has a thickness of at least 0.1 nm or at least 1 nm or at least 10 nm or at least 100 nm or at least 1 micron. The system of the present embodiments is further useful for microscopy of opaque samples. Thus, substance 14 is optionally and preferably opaque to the pump optical beam. Typically, the absorption thickness of substance 14 to the pump optical beam is at most 10 microns.

The pump optical beam that is generated by light source 20 is preferably selected to induce nonlinear excitation in substance 14. This can be done, for example, using focused pulses of light with sufficiently short (e.g., less than 100 ps or less than 50 ps or less than 10 ps) and with sufficiently high energy (e.g., above 100 pJ or above 500 pJ or above 1 nJ).

In various exemplary embodiments of the invention the pump optical beam is modulated. This can be achieved by an optical amplitude modulator 18 positioned on the optical path of beam 22. Modulator 18 can be a chopper wheel, a liquid crystal light modulator, an acousto-optical modulator, an electro-optical modulator and the like.

System 10 preferably comprises a measuring system 16 configured for measuring changes in a temperature-dependent or photo-excited property of substance 14.

The present embodiments contemplate many types of properties that can be measured by system 16. Representative examples include, without limitation, at least one property selected from the group consisting of thermoreflectance, luminescence, Raman shift, optical absorption, blackbody radiation and optical emission.

System 16 can measure the changes in the property optically or electrically. While the embodiments below are described with a particular emphasis to optical sensing of the changes in the property of substance 14, it is to be understood that more detailed reference to optical is not to be interpreted as excluding electrical sensing.

When system 16 employs optical sensing, a pulse of a probe optical beam 24 is preferably directed to the same spot as beam 22. Beam 24 can be generated by the same source 20 as beam 22. Alternatively, beam 24 can be generated by a different light source (not shown) that is synchronized with source 20. Beams 22 and 24 typically have different wavelengths. Preferably, a ratio between the central wavelength of the probe beam and the central wavelength of the pump beam is an integer (e.g., 2, 3 or 4).

In the schematic illustration of FIG. 1, which is preferred but is not to be considered as limiting, a beam generated by source 20 has a fundamental frequency and a harmonic (e.g., the second harmonic to ensure a ratio of 2 between the central wavelengths, or a third harmonic to ensure a ratio of 3 between the central wavelengths, or a fourth harmonic to ensure a ratio of 4 between the central wavelengths, etc). The beam is split by an optical splitter 28 (e.g., a dichroic filter or a dichroic mirror) into a beam having fundamental frequency and beam having the harmonic. Preferably, the former enacts pump beam 22 and the latter enacts probe beam 24, but the opposite configuration is also contemplated. At least one of beams 22 and 24 is redirected by a redirecting element, such as, but not limited to, a mirror (not shown) so that beams 22 and 24 propagate along separate optical paths.

In various exemplary embodiments of the invention there is a time-delay between beam 24 and beam 22. As demonstrated in the Examples section that follows, the present inventors found that a judicious selection of the time-delay can ensure super resolution microscopy beyond the diffraction limit. Preferably, beam 24 is delayed relative to beam 22. The time-delay between beams 24 and 22 is preferably less (e.g., at least 10 times or at least 100 times or at least 100 times less) than the pulse duration of the two beams. Representative examples of time delays suitable for the present embodiments include, without limitation, from about 100 fs to about 10 ps, or from about 100 fs to about 9 ps, or from about 100 fs to about 8 ps, or from about 100 fs to about 7 ps, or from about 100 fs to about 6 ps, or from about 100 fs to about 5 ps, or from about 100 fs to about 4 ps, or from about 100 fs to about 3 ps, or from about 100 fs to about 2 ps, or from about 100 fs to about 1 ps or less.

When both beams are generated by the same light source, the time-delay can be applied by an optical time-delaying element 26 positioned at the optical path of beam 24. Element 26 can apply the time-delay by guiding beam 24 through a longer optical path relative to beam 22, and/or through a higher refractive index as known in the art.

Following the optical processing of beams 22 and 24 (modulation of beam 22 and time-delay of beam 24, in the present example), beams 22 and 24 are preferably combined by an optical combiner 30 such that the beams are spatially overlapped. Optical combiner 30 can be any optical element that can receives light beams from separate optical paths and direct both beams to the same optical path. Representative examples for such an optical element include, without limitation, a dichroic filter and a dichroic mirror.

The overlapping beams are then directed to the same spot on substance 14. In the representative illustration of FIG. 1, the overlapping beams are redirected by a redirecting element 32, such as, but not limited to, a dichroic mirror or a dichroic filter, towards substance 14. The pump beam 22 interact with substance 14 to effect a change in one or more of its temperature-dependent or photo-excited properties, and the time-delayed probe beam 24 is used for measuring the effect. The probe beam interacts with substance 14, and is modified by the interaction, wherein the modification is indicative of the change in the property of the substance. The modified probe beam is reflected off substance 14 and can be transmitted into system 16, for example, via element 32 that can be configured to selectively transmit the reflected probe beam. System 16 includes a light sensor, such as, but not limited to, a photodiode, that converts the optical signal into an electrical signal that can be further processed by an electronic circuit.

In various exemplary embodiments of the invention system 16 is configured to measure the change of property within a predetermined spectral region of interest. The spectral region of interest is preferably selected so as to measure changes induced by non-linear excitation in substance 14. In some embodiments, system 16 is configured to detect the changes at a frequency which is an nth harmonic of the modulation of the pump beam, where n is an integer which is at least 2, e.g., 2, 3, 4, 5, 6, 7 or more. This can be achieved, for example, using a lock-in amplifier, as further detailed in the Examples section that follows.

System 10 preferably comprises an analysis system 34 configured for analyzing the measured changes to distinguish between information pertaining to the property at a portion 36 of spot 38, and information pertaining to the property at other portions 40 of spot 38. Typically, portion 36 is a central portion of spot 38 and portion 40 is peripheral with respect to portion 36.

The largest diameter of portion 36 of the spot is optionally and preferably less than the central wavelength of pump optical beam 22. In some embodiments of the present invention the largest diameter of portion 36 of the spot is less than half or less than 0.4 or less than 0.35 or less than 0.3 or less than 0.25 of the central wavelength of pump optical beam 22. When probe beam 24 is employed, the largest diameter of portion 36 of the spot is optionally and preferably less than the shortest central wavelength among the two beams (pump beam 22 and probe beam 24). In some embodiments of the present invention the largest diameter of portion 36 of the spot is less than half or less than 0.4 or less than 0.35 or less than 0.3 or less than 0.25 of the shortest central wavelength among the two beams.

Thus, when the spot size is, for example, diffraction limited, system 10 provides microscopy at a resolution which is beyond the diffraction limit.

The distinction between the information pertaining to the property at portion 36 and the information pertaining to the property at portions 40, is optionally and preferably achieved by detecting changes induced by the pump beam, and applying threshold to the detected changes such as to filter out changes induced by portions 40. In a representative example, a high pass filter is used so as to detect a portion of Raman scattering having sufficiently high frequency, and filter out the portions with low frequencies.

Figure 3:
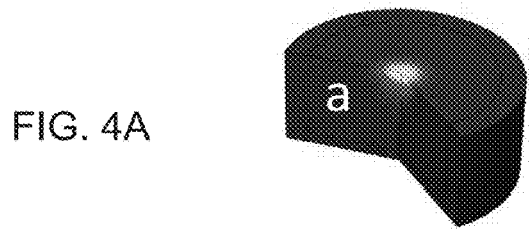

FIG. 3 is a flowchart diagram of a method of microscopy, according to some embodiments of the present invention. It is to be understood that several operations described below are optional and may not be executed.

The method begins at 50 and continues to 51 at which a pulse of a pump optical beam (e.g., beam 22) is directed to a substance (e.g., substance 14) to form an optical spot on the substance. The method continues to 52 at which changes in a temperature-dependent or photo-excited property of the substance are measured, electrically or optically as further detailed hereinabove. The method then proceeds to 53 at which the measured changes are analyzed to distinguish between information pertaining to the property at a portion of the spot (e.g., portion 36), and information pertaining to the property at other portions of the spot (e.g., portion 40), as further detailed hereinabove.

The method ends at 54.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

The present examples demonstrate a far-field label-free SR approach, which relies on the ability to photo-excite a spatial distribution of physical properties within a diffraction limited spot by an ultra-short laser pulse (pump). Reflectance of the photo-excited spot is probed, shortly after excitation, using a second laser pulse. SR is optionally and preferably achieved via detection of high order nonlinearities of the scanned reflectance image. The exemplified technique does not depend on fluorescent or any other form of labeling, and is suitable for various applications including, without limitation, the characterization of semiconductor and optoelectronic systems in any environment (vacuum, ambient, dry, wet) for transparent as well as opaque systems.

Photo-modulated reflectance can originate from numerous physical effects. In the present example, which is not to be considered as limiting, thermal excitation and the probing of thermoreflectance (TR) are considered.

TR, which records changes of reflectance upon heating, is typically used for measuring the thermal properties of materials, using linear models. The present inventors found that nonlinear components of TR can be used so as to narrow the effective point spread function (PSF).

In the present example, SR is demonstrated on Vanadium dioxide ($VO_2$), a material with strong reflectivity-nonlinearity to photo-excitation, and on silicon nanostructures. In silicon, minute, high order nonlinearities in TR are detected.

During a short period of time following photo-excitation, reflectance changes originate mainly from changes in carrier concentrations. Upon ultrafast photo-excitation, materials undergo several stages of relaxation before achieving thermal steady state; carrier excitation (10-100 fs) is followed by carrier-carrier and carrier-phonon scattering processes (10 fs-10 ps). Eventually, in a time scale of a few ps, the thermal transport can be treated classically. The instantaneous photo-excited spatial profile diffuses quickly and blurs in time. The present inventors demonstrated that in a ps timescale, it is possible to monitor the non-equilibrium state with high spatial resolution. The pump-probe time delay window is therefore judicially selected to achieve SR.

Figure 4A:
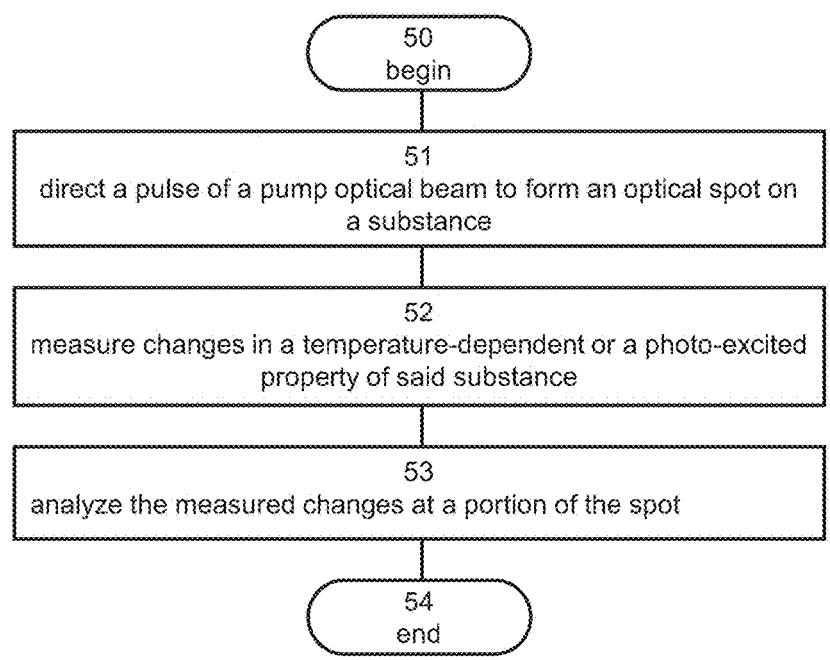
Figure 4B:
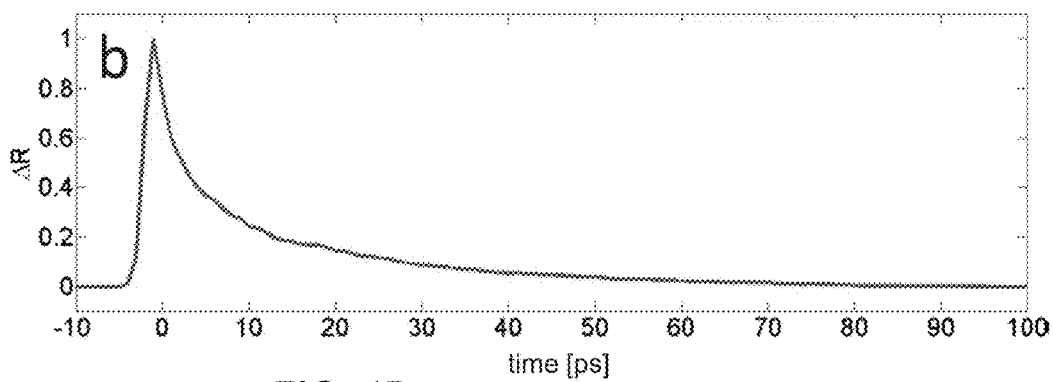
Figure 4C:
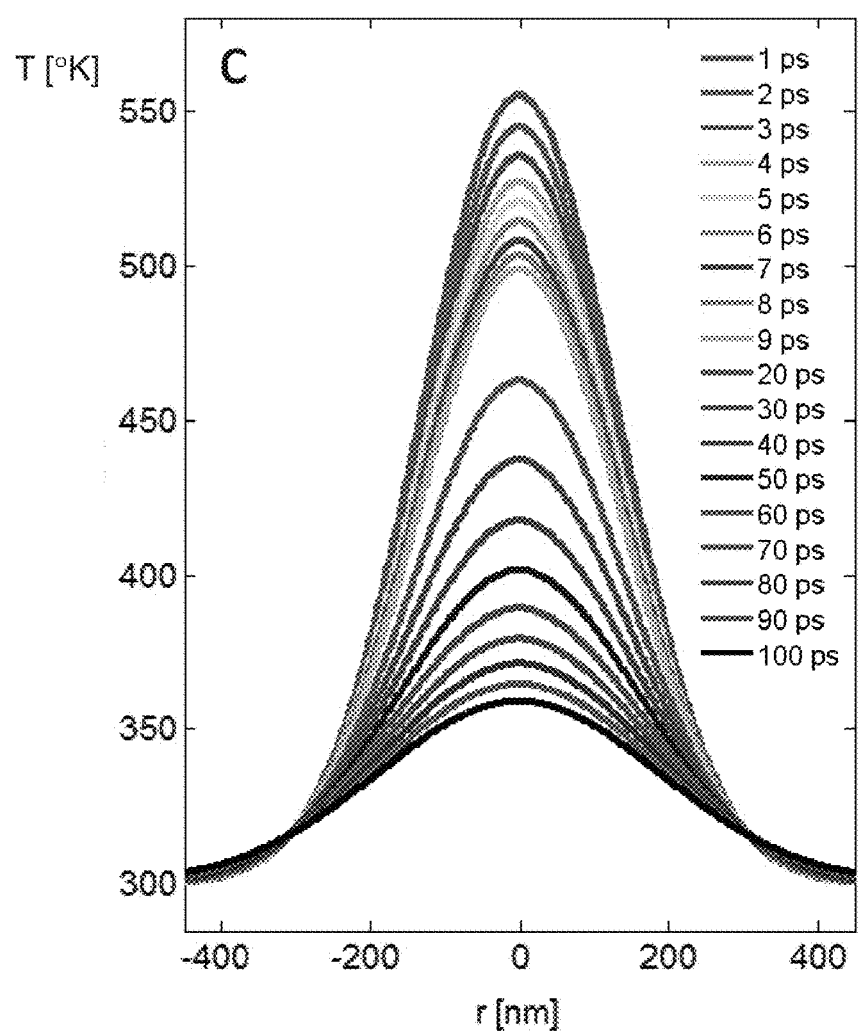
Figure 4D:
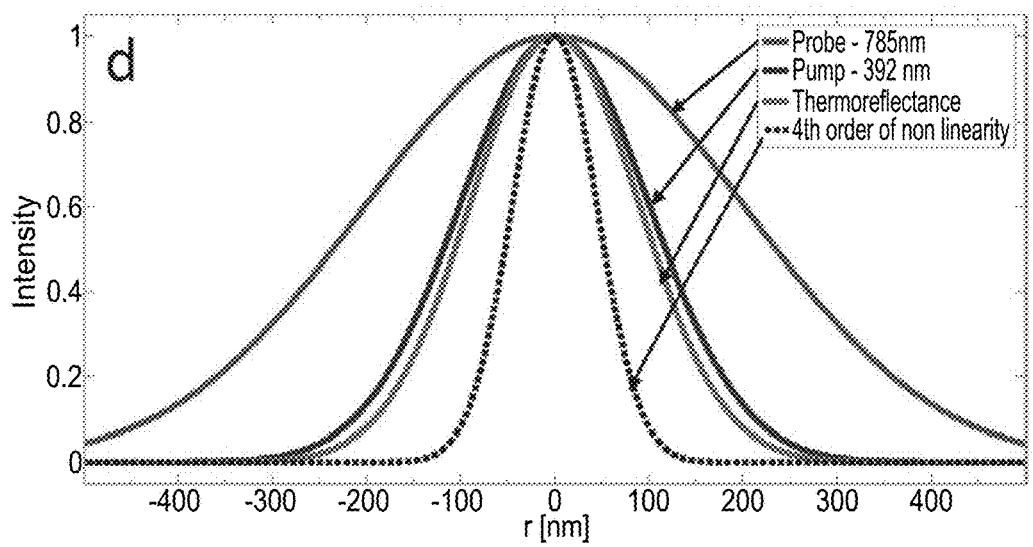

The principle of the SR technique exemplified in the present example is shown in FIGS. 4A-D. FIG. 4A shows results of simulation of optical absorption and temperature distribution in a silicon wafer at pump-probe delay of 1 ps. The pump fluence is about 70 mj/cm$^2$. The simulation details are provided below. FIG. 4B shows experimental dependence of thermo reflectance in silicon on the pump probe delay, FIG. 4C shows results of simulation of time dependent temperature profile in Silicon following photo-excitation, and FIG. 4D shows simulation of Point Spread function simulation. The curves in FIG. 4D correspond to probe pulse at 785 nm, pump at 392 nm, thermo reflectance at time-delay t=1 ps. In this case the PSF conforms to the product of the pump and the probe beam PSFs. Also shown is PSF resulting from 4th order nonlinearities in thermo reflectance.

Note that the initial spatial temperature distribution blurs and diminishes within few ps (see FIG. 4C), thus reducing spatial resolution.

A TR experimental setup used by the present inventors is illustrated in FIG. 5. A Ti-sapphire oscillator (Tsunami, Spectra physics) pumped by a 5 W 532 mn CW laser (Verdi, Coherent) was set to 1.5 ps pulse length at 785 nm central wavelength, with 10 nJ pulses at 80 MHz. The laser beam is passed through an optical isolator (Thorlabs, IO-5-780-HP) and focused by a 100 mm achromatic lens into a BBO crystal (L=5 mm) to produce second harmonic 392 nm pulses with 20% conversion efficiency.

The 785 nm beam enacted the probe and the second harmonic enacted the pump. The fundamental and 2$^{nd}$ harmonics beams were expanded and collimated by a 400 mm lens and split by a dichroic filter (Semrock BLP01-473R-25). Each beam was spatially filtered and further expanded. The time delay between pulses was adjusted by a variable delay line, using a retro-reflector, riding on a stepper motor translation stage (Standa 8MT175-100) with 1 µm resolution. The pump beam at 392 nm is modulated at 2.5 kHz using a chopper wheel. The pump and probe beams are combined by a dichroic mirror (Semrock SP01-785RU-25). The two spatially overlapped beams are focused by a 0.7NA air objective (Olympus LCPLFLN50×LCD) on the sample surface. The epi-reflected probe beam is transmitted through a dichroic filter (OD8 for the pump beam) and detected by the Trans-impedance silicon photodiode preamplifier (Thorlabs PDA100A) and a lock in amplifier (SRS 830). Timing was calibrated by the TR signal (see FIG. 17). Data was collected by an Analog to digital converted (NI usb-6000). Sample was scanned by an x-y stage, controlled with 10 nm resolution (Thorlabs DRV517 and BPC303).

The spatial resolution of linear TR where the pump and probe focused beams overlap in the focal plane was analyzed. The instantaneous temperature distribution was considered as indicative of the 3D absorption profile of the pump. Consequently, the PSF of the TR is the product of the PSFs of the pump and the probe. For Gaussian profiles for both beams, with $\sigma_{pump}$ and $\sigma_{probe}$ respectively, the resulting thermoreflectance profile is defined by:

$$\sigma_{TR} = \sqrt{\sigma_{pump}^2 \sigma_{probe}^2 / (\sigma_{pump}^2 + \sigma_{probe}^2)}.$$

For a pump beam with half the wavelength of the probe, resolution enhancement over electrically heated samples with the same diffraction-limited probe beam is By itself, this approach surpasses the Abbe diffraction limit. However, the present embodiments exploit the contributions of high order nonlinearities of TR to SR. For example, at Tc=340K, $VO_2$ undergoes a first-order structural phase transition (monoclinic to rutile) coinciding with an insulator-to-metal transition. Beyond critical pump fluence, $VO_2$ undergoes a photo-induced transition into a metallic state accompanied by a dramatic change in reflectivity within about 100 fs from excitation. Subsequently, electronic energy is transferred into lattice heating via electron-phonon coupling in ps time scales, and the volume of the thermally induced (non-coherent) phase transition expands. Later, heat diffusion cools the excited volume, and reversible phase transition into the insulator state occurs in hundreds of ps, at rates that depend inversely on the initial absorbed fluence.

These photo-thermal properties of $VO_2$ can be utilized according to some embodiments of the present invention to realize SR by tuning the pump laser energy to be slightly above the phase-transition treshhold. In these embodiments, only a portion of the spot generated by the pump beam (e.g., the intense center of the pump beam) induces the insulator-to-metal phase-transition, while other portions (e.g., the peripherial part of the beam) do not pass the transition threshold. The phase-transition invokes a sharp, non-linear response in the thermoreflectance and narrows the PSF beyond the diffraction limit.

The present inventors performed experiments on silicon layers patterned on sapphire, and on a patterned granular film of $VO_2$ (about 100 nm in thickness) on a silicon substrate.

The fabrication of silicon layers on sapphire sample was as follows. Stripes were prepared from 200 nm Si on Sapphire substrate. The pattern of 125 nm lines with variable distances (800-200 nm) was written by an e-beam system (Raith 150 EBL) on photoresist. After development, 40 nm film of Ni was deposited, followed by a lift off process. Si on Sapphire lines were prepared by dry etching in RIE (Nextral 860) using $CHF_3$ and $O_2$. Finally, the Ni capping was chemically etched in solution. The quality of the resulting samples was verified using a SEM (FEI Quanta 200 FEG). FIG. 9 is a SEM image of the obtained silicon on sapphire sample.

The fabrication of $VO_2$ sample was as follows. Vanadium dioxide ($VO_2$) structures were fabricated on silicon using electron beam lithography and pulsed laser deposition. Substrates were coated with about 150 nm of PMMA 495 A4 (Microchem) followed by a five minute bake at 180 C. A JEOL 9300FS electron beam lithography system operating at 100 kV was used to pattern the structures. MIBK/IPA 1:3 (Microchem) was used for development. Prior to deposition the patterned substrates were cleaned with $O_2$ plasma for 2 seconds. VO1.7 was deposited by PLD using a Epion PLD-3000 system with a Lambda Physik (Coherernt COMPex) excimer laser operating at 248 nm (KrF), with 4 $J/cm^2$ per pulse, with 25 Hz repetition rate and 25 ns pulse duration. Prior to deposition, the chamber was pumped down to $9 \times 10^{-6}$ Torr. Ablation of a pure vanadium metal target was performed in an ultra-high purity oxygen environment at $1.1 \times 10^{-2}$ Torr with a 2 sccm flow rate. The average deposition rate was 0.3 angstroms/second. Following deposition, liftoff was performed in Acetone. The patterned structures were annealed inside a tube furnace in 250 mTorr of $O_2$ at 723K for 10 minutes. Annealing under these conditions is necessary to crystallize the as-deposited $VO_{1.7}$ into switching $VO_2$. FIG. 10 is a SEM image of the obtained $VO_2$ sample.

The $VO_2$ sample comprises polycrystalline nanoparticles, and the phase transition may occur at somewhat different temperatures or laser fluences depending on nanoparticle size. Consequently, the contrast-visibility of the particles varies, as verified experimentally by the present inventors. The pump energy was tuned slightly above the onset of phase transition on individual $VO_2$ nanoparticles.

Figure 6A:
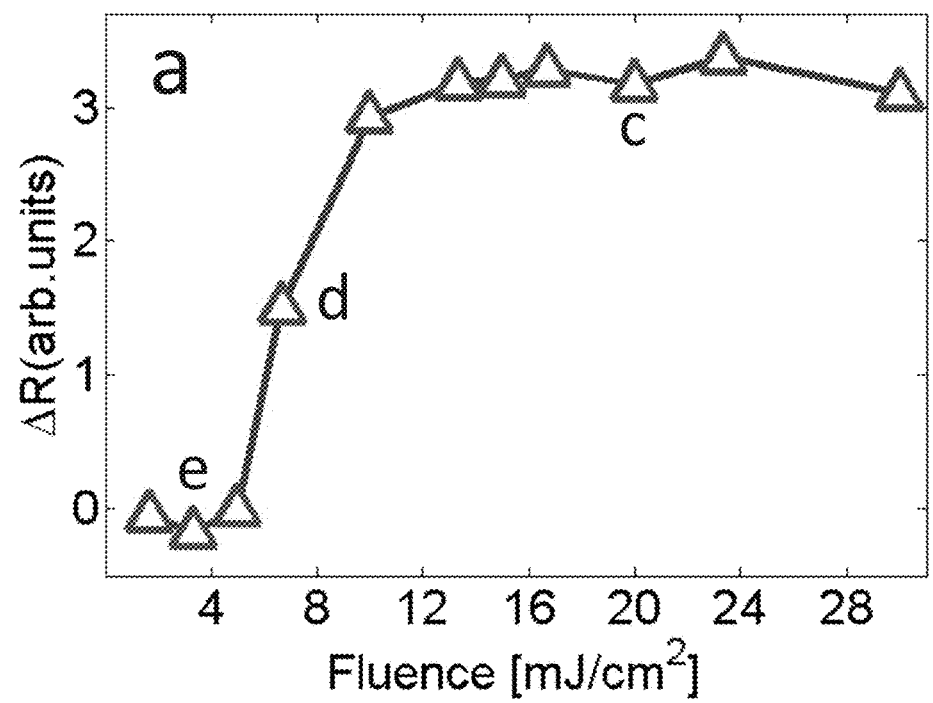
Figure 6B:
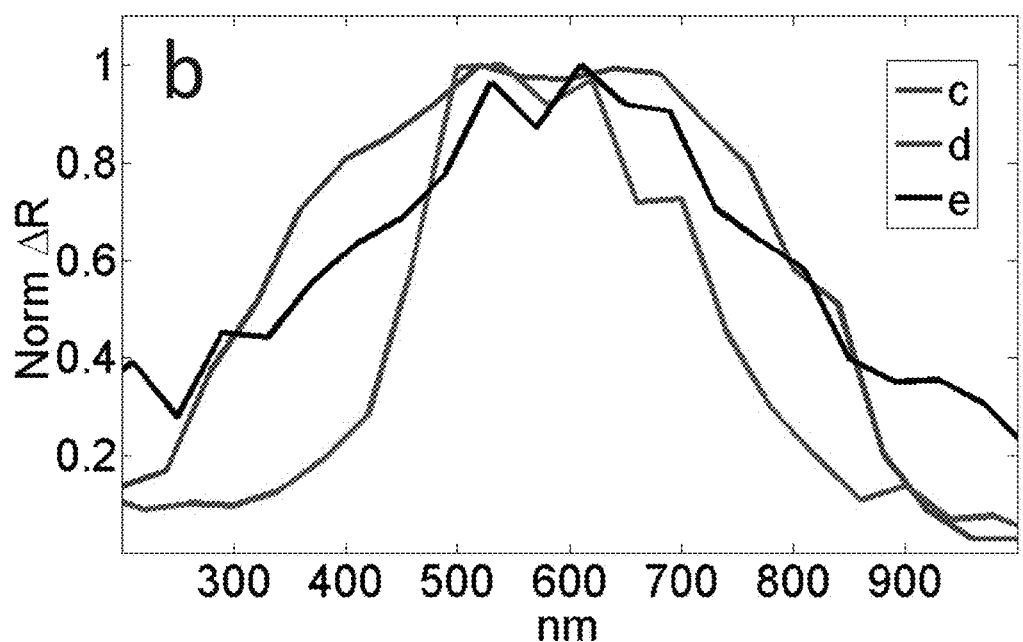
Figure 6C:
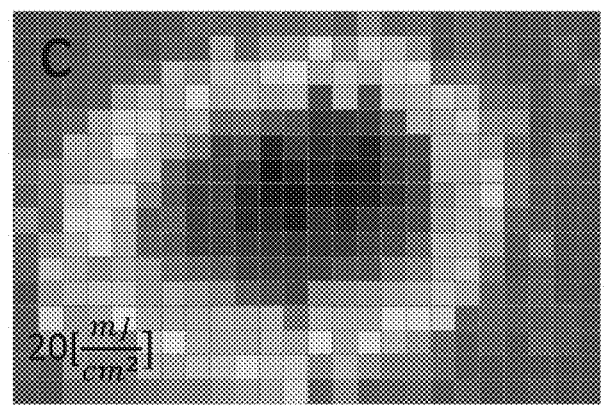
Figure 6D:
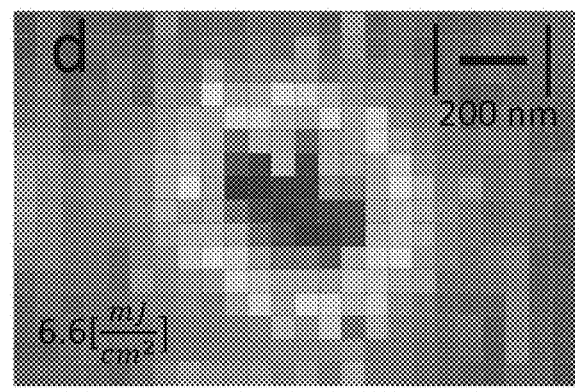
Figure 6E:
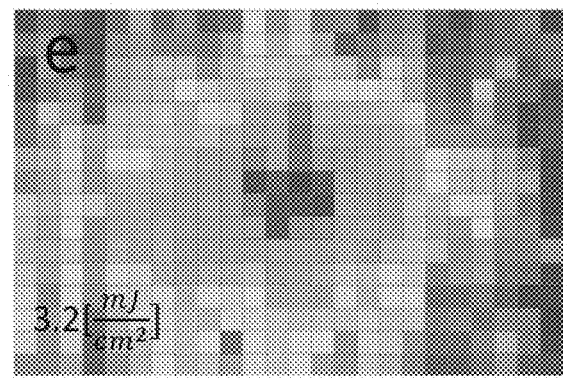

FIGS. 6A-E show TR characterization of a single $VO_2$ particle. In the characterization, a 270×200 nm $VO_2$ particle (size verified by SEM) was scanned with a series of pump fluence energies. FIG. 6A shows TR of the $VO_2$ particle as a function of the pump energy, and FIG. 6B shows normalized cross sections along x axis of the TR scans shown in FIGS. 6C, 6D and 6E. FIG. 6C shows a scan above phase transition (20 $mJ/cm^2$), FIG. 6D shows a scan at phase transition (6.6 $mJ/cm^2$), and FIG. 6E shows a scan below phase transition (3.2 $mJ/cm^2$). The pump-probe delay was 1 ps. The pump was modulated in a rectangular time wave form, with an amplitude that matches the optimal photo-excitation fluence.

Note the strong nonlinear response of TR to pump pulse energy. PSF of about 165 nm was achieved at pump energies slightly above the onset of the monoclinic-to-rutile phase transition (peak power 6.6 $mJ/cm^2$). At lower (3.2 $mJ/cm^2$) and higher (20 $mJ/cm^2$) energies, the particles appeared bigger (PSF of about 280 nm FWHM).

FIGS. 7A-C show results obtained from several $VO_2$ nanoparticles (pump intensity 8 $mJ/cm^2$), where FIG. 7A is a TR scan, FIG. 7B is a SEM image of the same area, and FIG. 7C shows the experimental results in comparison to simulation (the complete simulation input is shown in FIG. 15). In FIG. 7C, the sample was modeled (blue rectangles) as step function with longitudinal dimensions taken from the SEM image and heights proportional to the width in the SEM image to account for the higher reflection signal in wider particles.

Note that two particles with gap of 70 nm (corresponding to a PSF of 160 nm FWHM) were resolvable. A cross section in the TR scan has been fitted to the SEM image, convoluted with a Gaussian PSF. The best fit to the experimental data is the red curve of FIG. 7C. The black curve in FIG. 7C is a cross section of the TR scan along the line in FIG. 7A. The PSF was found to be between 160-190±10 nm (FWHM), about twice the diffraction limit of the pump. Note that the FWHM of the focused pump beam at 392 nm through a 0.7NA objective amounts to 290 nm (practically, 360 nm were measured). The range of PSFs values reflects the variability of the nanoparticles in respect to phase transition.

The above experimental results conform to the simulations, as further described below. Since the sign of TR of $VO_2$ is negative, opposite to the silicon substrate, the phase map provides a definition of device borders less than 10 nm.

In order to extract the nonlinear components of photo-modulated reflection from silicon nanostructures (at $\omega_m$), the reflection intensity at the corresponding harmonic frequencies ($\omega_m$, $2\omega_m$, $3\omega_m$, . . . ) was demodulated in a lock-in amplifier. In the present example, the origins of nonlinear effects in the TR of silicon were determined. Effects that contribute to nonlinearity include, multi-photon excitations or Auger recombination cooling.

Experiments were performed in accordance with some embodiments of the present invention on 100 nm thick silicon layers patterned on sapphire. At pump energy of about 100 mJ/cm$^2$, harmonic frequencies were found to be discernible in TR. The results are shown in FIGS. 8A-C. The estimated peak temperature of silicon at these conditions is about 700K. FIG. 8A shows a scan of double lines with gaps of 800-400 nm using the probe reflection only (Red), and the 1st (Black), 2nd (Purple), and 5th (Blue) harmonics of the modulated probe reflection. As shown, resolution is enhanced with higher harmonics. FIG. 8B is a HR-SEM image of the scanned sample. The silicon line width is 125 nm. The distances between lines are marked on the image (more data is shown in FIG. 16). FIG. 8C shows double lines scan with gaps of 370 and 280 nm using the 1st, 2nd, 5th and 7th harmonics, emphasizing the improvement on resolution.

Based on the SEM images of the patterned strips, the deconvoluted PSF of the 5$^{th}$ and 7$^{th}$ harmonic were found to be 230±10 nm, and 140±10 nm respectively, ×1.8 and ×3 narrower than the 1$^{st}$ harmonics respectively. In preferred embodiments of the present invention pure sine excitation is employed so as to reduce effects of direct excitation with higher harmonics. Without wishing to be bound to any particular theory, it is assumed that the lack of interference from direct excitation at this frequency accords for the good resolution of the seventh harmonics. The resolution improvement is theoretically limited only by the SNR.

The present Examples demonstrate a concept for SR imaging by utilizing the nonlinear response of TR. The present Examples show the applicability of the inventive technique to VO$_2$ and silicon nanostructures. The technique of the present embodiments can be applied to additional materials and exploit any physical properties that depend on temperature, such as luminescence, Raman shift, absorption and the like.

Definition of PSF and SR in the Photo-Modulated Image

The image resolution in case of a linear TR is determined by the pump beam intensity profile, the time delay between the pump, the probe intensity profile and the scanned object. In the analysis presented herein, the temperature profile is considered to be identical to the laser Gaussian fluence distribution. This consideration is applicable for sufficiently short pump-probe delay, for example, about 0-3 ps. The probe has its own Gaussian shape. Consequently, the linear TR image, P(x,y), comprises of the product of the pump and the probe, convoluted with the object O(x,y).

$$P(x, y) = PSF_{pump} * PSF_{probe} \otimes O(x, y) =$$

$$PSF_{TR} \otimes O(x, y) = I_{pump} e^{\frac{r^2}{2\sigma_{pump}^2}} I_{probe} e^{\frac{r^2}{2\sigma_{probe}^2}} (t = 0) \otimes O(x, y)$$

Hence the effective PSF in the linear thermo-reflectance, PSF$_{TR}$, can be extracted by deconvoluting the image with the object resulting in a Gaussian with standard deviation of:

$$\sigma_{TR} = \sqrt{\sigma_{pump}^2 \sigma_{probe}^2 / (\sigma_{pump}^2 + \sigma_{probe}^2)}$$

The resolution enhancement criterion used herein in the linear case will now be explained. For a pump beam with half the wavelength of the probe, resolution enhancement over electrically heated samples with the same diffraction-limited probe beam is $\sqrt{5}$. In the case of pump and probe with nearly identical wavelength this improvement is $\sqrt{2}$. Incorporating non linearities induced by the pump improves the resolution further, beyond the linear case.

VO$_2$ introduces a non-linear thermo reflectance response function to optical excitation in the vicinity of its phase transition. FIGS. 11A and 11B show results of simulation of VO$_2$ PSF when excitation fluence is in the onset of phase-transition. FIG. 11B shows the changes in reflectivity $\Delta R(\Phi)$ as a function of pump fluence. Note the significant change in reflectivity as the fluence reaches the phase transition at about 7 mJ/cm$^2$. FIG. 11A shows $\Phi(r)$ a diffraction limited pump with maximal fluence of 7 mJ/cm$^2$ (blue), and $\Delta R(r)$, the photo-modulated reflectivity PSF of the probe (green), where $\Delta R(r) = R(\Phi(r))$ is the product of the blue curve with the 8th order polynomial fit.

Based on the dependence of reflectivity on the pump pulse fluence $\Delta R(\Phi)$, the effective PSF of the TR was simulated. The maximum fluence of the pump was optimized for SR and selected to be 7 mJ/cm$^2$. For each spatial coordinate, r, in the pump Gaussian fluence profile $\Phi(r)$, a local reflectivity value was attributed according to the calibration curve. $\Delta R(r) = \Delta R(\Phi(r))$. This transformation yielded the effective PSF in VO$_2$ samples (green curve in FIG. 11A).

This simulation can be applied in cases in which the phase transition and reflectivity changes are local. A representative example is polycrystalline nanoparticles.

The present inventors found that the sharpest PSFs correspond to pump energies of 6-8 mJ/cm$^2$. FIG. 12 compares the effective PSF of VO$_2$, excited with fluence of 7 mJ/cm$^2$ to the probe, the pump and the 4th order non-linearity of the pump Gaussian beam, which provides similar resolution. This simulation shows that the phase transition of VO$_2$ improves the resolution of the technique of the present embodiments in another factor of 2, in agreement with the experimental results presented above.

For silicon, the higher orders of non-linearity in silicon, measured by the higher modulation harmonic, can be describe in the following formalism. The non-linear reflectivity can be represented as a Taylor series $\Delta R/R = a_0 T + a_1 T^2 + a_2 T^3 + \ldots$ For pure sinusoidal pump excitation, the temperature is also a harmonic function, $T(\alpha) = I b_0 \exp(i\omega_m t)$, where $\omega_m$ is the modulation frequency of the pump excitation. The thermo reflectance $\Delta R/R$ is $$\frac{\Delta R}{R} \approx a_0 I e^{i\omega_m t} + a_1 I^2 e^{i2\omega_m t} + a_2 I^3 e^{i3\omega_m t} \ldots$$

Therefore the nonlinearity is measured by detection the nth modulation harmonics, where n is an integer of at least 2.

The nonlinear intensity profile is a Gaussian in the power of (n=2, 3 . . . ) and therefore the modulation harmonics order corresponds to Gaussian multiplication leading to enhanced resolution, as simulated and depicted in FIG. 13.

This simulation represents a case in which the modulation is a pure harmonic wave. The results show a trend of resolution improvement with higher order on non-linearity. When the excitation is not purely sinusoidal, the resolution is lower due to the mixing of the nonlinear response and the direct excitation with high harmonics. Generally, for a photo-modulated reflectance of the nth order in modulation frequency for a nearly identical wavelength pump and probe the resolution is expected to improve by a factor of about $\sqrt{n+1}$.

Phase Image of the VO$_2$ on Silicon Thermo Reflectance

The lock-in phase image of TR in VO$_2$ on silicon samples show very abrupt phase switching. The thermo reflectance coefficient of silicon is positive whereas the VO$_2$ coefficient is negative. When scanning the edge of VO$_2$ surface on silicon device, the zero crossing of the thermo reflectance phase serves as a balance detector with resolution better than the scan step size (<10 nm). This allows precision determination of borders of devices with dimensions which are in the order of the spot size or larger.

FIG. 14 shows line scan of patterned VO$_2$ on silicon. The Gray rectangular show the location of VO$_2$ on the silicon surface amplitude (R), phase ($\phi$)) and X=R cos $\phi$ lock in amplifier signals. The change of sign in X and the fast change of phase on the transition from a VO$_2$ surface to the silicon surface.

Pulse Heating Estimate

In the aforementioned silicon experiment, the signal of high order non-linearities is enhanced with increased laser fluence. In some embodiment, it is desirable to restrict heating of the inspected sample, for example, to avoid or reduce damage. In this section, the temperature increase during photo-excitation of silicon in the TR experiments is calculated. It will be shown that it the temperature increase is well below the melting point of silicon ($\Delta T \approx 485K$). Total cooling of the sample between pulses, 12.5 ns apart, is simulated and verified experimentally. Post measurement damage inspections were performed by optical microscopy and SEM. No discernible damage was identified.

The pump at 392 nm and measured pulse energy, $E_{pulse}=0.04\pm0.01$ nJ (after the objective) is focused to a diffraction limited Gaussian spot (250 nm FWHM) and absorbed ~100 nm near the surface (absorption coefficient, $\alpha=10^5$ cm$^{-1}$). The maximum energy fluence, $\Phi_{(r=0)}$ at the center of the spot was estimated to be ~260 Jm$^{-2}$, using the relation:

$$\Phi_{(r=0)} = \frac{E_{pulse}}{2\pi \int_0^\infty e^{-\left(\frac{r^2}{2\sigma^2}\right)} r dr}$$

In this example, total conversion of carrier excess energy to heat is assumed. It is further assumed that the band gap energy is conserved and not converted to heat within the pump-probe delay time. The following values were used to estimate the surface temperature rise in the center of the Gaussian beam immediately after laser photo-excitation:

Reflectivity of silicon at 392 nm R=0.5; Density $$\rho = 2330 \frac{Kg}{m^2};$$

Heat capacity $$C_p = 703 \frac{J}{Kg * K^D}.$$

Accordingly:

$$\Delta T_{(r=0)} \approx \frac{\Phi_{(r=0)} * \alpha}{\rho C_p} * (1-R) * \left(1 - \frac{\text{Band Gap}}{\text{Photon Energy}}\right) = 485° K \pm 100 K$$

The same analysis was performed to the probe beam, with much larger effective heated volume, mainly, due to the smaller absorption coefficient in 785 nm, $\alpha=10^3$ cm$^{-1}$. Temperature rise by the probe beam is estimated to be $\Delta T_{probe} \approx 5°$ K.

Heat Conduction Simulation

Time dependent heat conduction simulations were performed using the commercial finite element solver COMSOL® (heat transport module) to evaluate the spatial temperature spread, due to heat diffusion, over time. The laser beam absorption created a heat source, Q(r,z,t), represented by:

$$Q(r,z,t) = \int_{t=0}^{1ps} I(t) * e^{\alpha(z-z0)} * G(r) * (1-R) dt$$

Where l(t) is the laser intensity, $\alpha=10^5$ cm$^{-1}$ is the absorption coefficient along the z axis of the sample, G(r) is the diffraction limited Gaussian intensity profile, R is the reflectivity, and the pulse is defined between t=0 and t=1 ps. Effect of two photon absorption was neglected. After the pulse, heat diffusion was propagated without any heat source. Thermal conductivity $$K = 163 \frac{W}{mK^0}$$

was used in the simulations along with the other parameters defined in FIGS. 15 and 16.

Temporal and Spatial Overlap of the Beams

In this example, TR measurements were used for initial timing of the pump and probe, after the objective. It is advantageous to use TR for timing the pulses since it is performed directly on the sample and not effected by any dispersions in the optical system. Moreover, the TR was used for optimizing the spatial beam overlap. A kinematic piezoelectric actuator (POLARIS-K1PZ) was used to finely tune the overlap of the beams. The following graph depicts the time resolved TR on silicon wafer and VO$_2$ surface.

FIG. 17 shows time resolved reflectance of silicon and VO$_2$. The pump excitation fluences for Si and VO$_2$ are 70 mJ/cm$^2$ and 13 mJ/cm$^2$, respectively. The time-delay is 1 ps.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] Lewis, A. et al. Near-field optics: from subwavelength illumination to nanometric shadowing. Nat. Biotechnol. 21, 1378-86 (2003).

[2] Klar, T. a, Jakobs, S., Dyba, M., Egner, a & Hell, S. W. Fluorescence microscopy with diffraction resolution barrier broken by stimulated emission. Proc. Natl. Acad. Sci. U.S.A 97, 8206-10 (2000).
[3] Klar, T a, Engel E, Hell S, W. Breaking Abbe's diffraction resolution limit in fluorescence microscopy with stimulated emission depletion beams of various shapes. Phys. Rev. E 64, (2001).
[4] Henriques, R., Griffiths, C., Hesper Rego, E. & Mhlanga, M. M. PALM and STORM: unlocking live-cell super-resolution. Biopolymers 95, 322-31 (2011).
[5] Rust, M. J., Bates, M. & Zhuang, X. imaging by stochastic optical reconstruction microscopy (STORM). Nat. Methods 3, 793-795 (2006).
[6] Fujita, K., Kobayashi, M., Kawano, S., Yamanaka, M. & Kawata, S. High-Resolution Confocal Microscopy by Saturated Excitation of Fluorescence. Phys. Rev. Lett. 99, 228105 (2007).
[7] Gustafsson, M. G. Surpassing the lateral resolution limit by a factor of two using structured illumination microscopy. J. Microsc. 198, 82-7 (2000).
[8] Dertinger, T., Colyer, R., Iyer, G., Weiss, S. & Enderlein, J. fluctuation imaging (SOFI). Proc. Natl. Acad. Sci. 106, 22287-22292 (2009).
[9] Schwartz, O. et al. Superresolution microscopy with quantum emitters. Nano Lett. 13, 5832-6 (2013).
[10] Wang, P. et al. Far-field imaging of non-fluorescent species with subdiffraction resolution. Nat. Photonics 7, 449-453 (2013).
[11] Nedosekin, D. a, Galanzha, E. I., Dervishi, E., Biris, A. S. & Zharov, V. P. Super-resolution nonlinear photothermal microscopy. Small 10, 135-42 (2014).
[12] Barsi, C. & Fleischer, J. W. Nonlinear Abbe theory. Nat. Photonics 7, 639-643 (2013).
[13] Zalevsky, Z. Nonlinear optics: Defying Abbe's law. Nat. Photonics 7, 593-594 (2013).
[14] Bogdanowicz, J. Fundamental Study of Photomodulated Optical Reflectance towards Non-Destructive Carrier Profiling in Silicon. (2011).
[15] Cahill, D. G. Analysis of heat flow in layered structures for time-domain thermoreflectance. Rev. Sci. Instrum. 75, 5119-5122 (2004).
[16] Cahill, D. G. et al. Nanoscale thermal transport. J. Appl. Phys. 93, 793 (2003).
[17] Mazur, E. Interaction of Ultrashort Laser Pulses with Solids. 1-54 (1996).
[18] Sundaram, S. K. & Mazur, E. Inducing and probing non-thermal transitions in semiconductors using femtosecond laser pulses. Nat. Mater. 1, 217-24 (2002).
[19] Morin, F. J. Oxides which show a metal-to-insulator transition at the neel temperature. Phys. Rev. Lett. 3, 34-36 (1959).
[20] Basov, D. N., Averitt, R. D., van der Marel, D., Dressel, M. & Haule, K. Electrodynamics of correlated electron materials. Rev. Mod. Phys. 83, 471-541 (2011).
[21] Pashkin, a. et al. Ultrafast insulator-metal phase transition in VO2 studied by multiterahertz spectroscopy. Phys. Rev. B 83, 195120 (2011).
[22] Kübler, C. et al. Coherent Structural Dynamics and Electronic Correlations during an Ultrafast Insulator-to-Metal Phase Transition in VO2. Phys. Rev. Lett. 99, 116401 (2007).
[23] Wall, S. et al. Tracking the evolution of the electronic and structural properties of VO 2 during the ultrafast photoinduced insulator-metal transition. Phys. Rev. B 87, (2013).
[24] Lopez, R., Haynes, T., Boatner, L., Feldman, L. & Haglund, R. Size effects in the structural phase transition of VO2 nanoparticles. Phys. Rev. B 65, 224113 (2002).
[25] Kar, A. et al. Probing Ultrafast Carrier Dynamics in Silicon Nanowires. IEEE J. Sel. Top. Quantum Electron. 17, 889-895 (2011).
[26] Hopkins, P. E. et al. Excitation rate dependence of Auger recombination in silicon. J. Appl. Phys. 107, 053713 (2010).

What is claimed is:

1. A method of microscopy, comprising:
   directing a pulse of a pump optical beam to form an optical spot on a substance;
   measuring changes in a temperature-dependent or photo-excited property of said substance; and
   analyzing said measured changes to distinguish between information pertaining to said property at a portion of said spot, and information pertaining to said property at other portions of said spot;
   wherein a largest diameter of said portion of said spot is less than a central wavelength of said pump optical beam.

2. The method according to claim 1, wherein said pump optical beam is selected to induce nonlinear excitation in said substance.

3. The method according to claim 2, wherein said pump optical beam has a pulse duration of less than 100 ps and energy above 100 pJ.

4. The method according to claim 1, wherein a spectral region of interest is selected so as to measure changes induced by non-linear excitation in said substance.

5. The method according to claim 1, wherein said measuring comprises detecting changes induced by said pump beam, and applying threshold to said detected changes such as to filter out changes induced by said other portions of said spot.

6. The method according to claim 1, wherein said pump optical beam is modulated.

7. The method according to claim 6, wherein said measuring comprises detecting said changes at a frequency which is an nth harmonic of said modulation, said n being at least 2.

8. The method according to claim 1, wherein a largest diameter of said portion of said spot is less than 0.4 of a central wavelength of said pump optical beam.

9. The method according to claim 1, wherein said measuring is by a pulse of a probe optical beam.

10. The method according to claim 9, wherein a largest diameter of said portion of said spot is less than a shortest central wavelength among said pump optical beam and said probe optical beam.

11. The method according to claim 9, wherein a time delay between said probe pulse and said pump pulse is less than 10 ps.

12. The method according to claim 9, wherein a ratio between central wavelengths of said probe and said pump optical beams is an integer.

13. The method according to claim 9, wherein said probe optical beam and said pump optical beam are generated by the same source, but are directed to said substance via different optical paths.

14. The method according to claim 1, wherein said measuring is executed electrically.

15. The method according to claim 1, wherein said temperature-dependent property comprises a property selected from the group consisting of thermoreflectance, luminescence, Raman shift, optical absorption, optical emission and blackbody radiation.

16. The method according to claim 1, wherein said substance is inorganic.

17. The method according to claim 1, wherein said substance is organic.

18. The method according to claim 1, wherein said substance is not functionally labeled.

19. The method according to claim 1, wherein said substance is solid.

20. The method according to claim 1, wherein said substance is dry.

21. The method according to claim 1, wherein said substance is wet.

22. The method according to claim 1, being executed in vacuum.

23. The method according to claim 1, being executed in gaseous environment.

24. The method according to claim 1, being executed in liquid environment.

25. The method according to claim 1, wherein said substance has a thickness of at least 0.1 nm.

26. The method according to claim 1, wherein said substance has a thickness of at least 0.1 nm.

27. The method according to claim 1, wherein said substance is opaque to said pump optical beam.

28. The method according to claim 1, wherein an absorption thickness of said substance to said pump optical beam is at most 10 micron.

29. A system of microscopy, comprising:
an optical system configured for directing a pulse of a pump optical beam to form an optical spot on a substance;
a measuring system configured for measuring changes in a temperature-dependent or photo-excited property of said substance; and
an analysis system configured for analyzing said measured changes to distinguish between information pertaining to said property at a portion of said spot, and information pertaining to said property at other portions of said spot;
wherein a largest diameter of said portion of said spot is less than a central wavelength of said pump optical beam.

* * * * *